US006861575B2

(12) United States Patent
Falco

(10) Patent No.: US 6,861,575 B2
(45) Date of Patent: Mar. 1, 2005

(54) ASPARTATE KINASE

(75) Inventor: Saverio Carl Falco, Arden (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 182 days.

(21) Appl. No.: 09/890,813

(22) PCT Filed: Dec. 19, 2000

(86) PCT No.: PCT/US00/34396

§ 371 (c)(1),
(2), (4) Date: Aug. 2, 2001

(87) PCT Pub. No.: WO01/46393

PCT Pub. Date: Jun. 28, 2001

(65) Prior Publication Data

US 2002/0183486 A1 Dec. 5, 2002

Related U.S. Application Data

(60) Provisional application No. 60/172,944, filed on Dec. 21, 1999.

(51) Int. Cl.⁷ .......................... A01H 1/00; C07H 21/04; C07K 14/415; C12N 5/14; C12N 9/00

(52) U.S. Cl. .......................... 800/295; 435/6; 435/69.1; 435/468; 435/419; 435/252.3; 435/320.1; 530/370; 536/23.6; 800/278

(58) Field of Search .......................... 435/6, 69.1, 468, 435/419, 252.3, 320.1; 530/370; 536/23.6; 800/278, 295

(56) References Cited

U.S. PATENT DOCUMENTS

| 5,258,300 A | 11/1993 | Glassman et al. |
| 5,451,516 A | 9/1995 | Matthews et al. |
| 5,773,691 A | 6/1998 | Falco et al. |
| 6,459,019 B1 | 10/2002 | Falco et al. |

FOREIGN PATENT DOCUMENTS

EP  O 485 970 A2  5/1992

OTHER PUBLICATIONS

EMBL Sequence Library Database Accession NO: 023653, Jan. 1, 1998, Tang G. et. al., Cloning and Expression of an *Arabidopsis thaliana* cDNA Encoding a Monofunctional Aspartate Kinase Homologous to the Lysine–Sensitive Enzyme of *Escherichia coli*.
Guilang Tang et. al., Plant Molecular Biology, vol. 34;287–294, 1997, Cloning and Expression of an *Arabidopsis thaliana* cDNA Encoding a Monofunctional Aspartate Kinase Homologous to the Lysine–Sensitive Enzyme of *Escherichia coli*.
EMBL Sequence Library Databse Accession NO: AF135862, Jul. 1, 1999, Esau B. D. et. al., Isolation and Characterization of a cDNA Clone Encoding a Monofunctional Aspartokinase.
EMBL Sequence Library Database Accession NO: Q9XHCS, Nov. 1, 1999, Esau B. D. et. al., Isolation and Characterization of a cDNA Clone Encoding a Monofunctional Aspartokinase.
EMBL Sequence Library Database Accession NO: AB042521, May 12, 2000, Kiyota S., Lysine Sensitive Aspartate Kinase Kinase From Rice.
EMBL Sequence Library Database Accession NO: Q9MAX0, Oct. 1, 2000, Kiyota S., Lysine Sensitive Aspartate Kinase From Rice.
Hagai Karchi et. al., The Plant Journal, vol. 3:721–727, 1993, Seed–Specific Expression of a Bacterial Desensitized Aspartate Kinase Increases the Production of Seed Theronine and Methionine in Transgenic Tobacco.
John Giovanelli et al., Plant Phys., vol. 77:450–455, 1985, In vivo Regulation of De Novo Methionine Biosynthesis in a Higher Plant (Lemna).
Faith C. Belanger and Alan L. Kriz, Plant Phys., vol. 91:636–643, 1989, Molecular Characterization of the Major Maize Embryo Globulin Encoded by the GLB1 Gene.
R. L. Phillips et. al., Cereal Chem., vol. 62:213–218, 1985, Elevated Protein–Bound Methionine in Seeds of a Maize Line Resistant to Lysine Plus Threonine.
James T. Madison et. al., Plant Cell, vol. 7:473–476, 1988, Characterization of Soybean Tissue Culture Cell Lines Resistant to Methionine Analogs.
National Center for Biotechnology Information General Identifier NO: 7798569, May 13, 2000, Kiyota, S., Lysine Sensitive Aspartate Kinase from Rice.
National Center for Biotechnology Information General Identifier NO: 4376158, Jul. 2, 1997, Frankard, V. et al., Molecular characterization of an *Arabidopsis thaliana* cDNA coding for a monofunctional aspartate kinases.
National Center for Biotechnology Information General Identifier NO: 7529283, Apr. 7, 2000, Bevan, M. et al.
National Center for Biotechnology Information General Identifier NO: 5305740, Jun. 24, 1999, Esau, B. D., et al., Isolation and Characterization of a cDNA Clone Encoding a Monofunctional Aspartokinase.
J. Theze et. al., Journal of Bacteriology, vol. 117:133–143, 1974, Mapping of the Structural Genes of the Three Aspartokinases and of the Two Homoserine Dehygrogenases of *Escherichia coli* K–12.
Valerie Frankard et. al., Plant Molecular Biology, vol. 34:233–242, 1997, Molecular Characterization of an *Arabidopsis thaliana* cDNA Coding for a Monofunctional Aspartate Kinase.
EMBL Sequence Library Database Accession NO: X98873, Jul. 2, 1997, Frankard V. et. al., Molecular Characterisation of an *Arabidopsis thaliana* cDNA Coding for a Monofunctional Aspartate Kinase.

(List continued on next page.)

*Primary Examiner*—Phuong T. Bui

(57) ABSTRACT

This invention relates to an isolated nucleic acid fragment encoding an aspartate kinase. The invention also relates to the construction of a chimeric gene encoding all or a portion of the aspartate kinase, in sense or antisense orientation, wherein expression of the chimeric gene results in production of altered levels of the aspartate kinase in a transformed host cell.

12 Claims, 2 Drawing Sheets

OTHER PUBLICATIONS

EMBL Sequecne Library Database Accession NO: O23152, Jan. 1, 1998, Frankard V. et. al., Molecular Characterization of an *Arabdopsis thaliana* cDNA Coding for a Monofunctional Aspartate Kinase.

EMBL Sequence Library Database Accession NO: U62020, Jul. 16, 1997, Tang G. et. al., Cloning and Expression of an *Arabidopsis thaliana* cDNA Encoding a Monofunctional Aspartate Kinase Homologous to the Lysine–Sensitive Enzyme of *Escherichia coli*.

S. C. Falco et al., Transgenic Canola and Soybean Seeds with Increased Lysine, BioTechnology, Jun., 1995, vol. 13.

U.S. Appl. No. 09/049,304, Falco et al., filed Mar. 27, 1998.

U.S. Appl. No. 10/804,678, Falco et al., filed Mar. 19, 2004.

U.S. Appl. No. 10/023,066, Falco, filed Dec. 17, 2001.

FIGURE 1A

```
                             *         *         *         *         *         *
SEQ ID NO:06    MAIPVRSAAAPR-RLVPSIPPASSGHV----RGLACFGTRTGPRGARGLSMVVADSTSRR
SEQ ID NO:08    MAIPVRSAAAPR-RLVPSIPPASSGHV----RGLACFGTRTGPRGARGLSMVVADSTSRR
SEQ ID NO:17    MASALQQLQGVQGKLAVSMSVRRSLHHCKSQIGFAALGAPVCARRVWGNRVAFSVTTCK-
                1                                                          60

*         *         *         *         *         *
SEQ ID NO:06    AKQADGGDGVLGAPVLGGLGMEGLGDQLSVVMKFGGSSVSSAARMAEVAGLILTFPEERP
SEQ ID NO:08    AKQADGGDGVLGAPVLGGLGMEGLGDQLSVVMKFGGSSVSSAARMAEVAGLILTFPEERP
SEQ ID NO:17    ---ASTSDVIEKNATENGMVSSEGETSFTCVMKFGGSSVASADRMKEVATLILSFPEERP
                61                                                        120

*         *         *         *         *         *
SEQ ID NO:06    VVVLSAMGKTTNNLLLAGEKAVGCGVIHVSEIEEWNMVKSLHIKTVDELGLPX-ICNTSL
SEQ ID NO:08    VVVLSAMGKTTNNLLLAGEKAVGCGVIHVSEIEEWNMVKSLHIKTVDELGLPRSVIQDML
SEQ ID NO:17    IVVLSAMGKTTNKLLLAGEKAVSCGVINVSSIEELCFIKDLHLRTVDQLGVDGSVISKHL
                121                                                       180

*         *         *         *         *         *
SEQ ID NO:06    YELEQLLKGIAMMKELTPRTSDYLVSFGECMSTRIFSAYLNKIRVKARQYDAFDIGFITT
SEQ ID NO:08    DELEQLLKGIAMMKELTPRTSDYLVSFGECMSTRIFSAYLNKIRVKARQYDAFDIGFITT
SEQ ID NO:17    EELEQLLKGIAMMKELTKRTQDYLVSFGECMSTRIFAAYLNKIGVKARQYDAFEIGFITT
                181                                                       240

*         *         *         *         *         *
SEQ ID NO:06    DEFGNADILEATYPAVAKRLHGDWIQDPAIPVVTGFLGKGWKSGAVTTLGRGGSDLTATT
SEQ ID NO:08    DEFGNADILEATYPAVAKRLHGDWIQDPAIPVVTGFLGKGWKSGAVTTLGRGGSDLTATT
SEQ ID NO:17    DDFTNADILEATYPAVAKRLHGDWLSDPAIAIVTGFLGKARKSCAVTTLGRGGSDLTATT
                241                                                       300
```

FIGURE 1B

```
SEQ ID NO:06    IGKALGLREIQVWKDVDGVLTCDPNIYPHAKTVPYLTFEEATELAYFGAQVLHPQSMRPA
SEQ ID NO:08    IGKALGLREIQVWKDVDGVLTCDPNIYPHAKTVPYLTFEEATELAYFGAQVLHPQSMRPA
SEQ ID NO:17    IGKALGLPEIQVWKDVDGVLTCDPNIYPKAEPVPYLTFDEAAELAYFGAQVLHPQSMRPA
                301                                                       360

SEQ ID NO:06    REGDIPVRVKNSYNPKAPGTLITRQRDMDXGLVVLTSIVLKSNVTMLDIVSTRMLGQYGF
SEQ ID NO:08    REGDIPVRVKNSYNPKAPGTLITRQRDMDK--VVLTSIVLKSNVTMLDIVSTRMLGQYGF
SEQ ID NO:17    RESDIPVRVKNSYNPKAPGTLITKARDMSKA--VLTSIVLKRNVTMLDIASTRMLGQYGF
                361                                                       420

SEQ ID NO:06    LARVSGICYIEDLCISVDCVATSEVSVSVSLDPSKIWSRELIQQASELDHVVEELEKIAI
SEQ ID NO:08    LARVFAI--FEDLCISVDCVATSEVSVSVSLDPSKIWSRELIQQ--ELDHVVEELEKIAI
SEQ ID NO:17    LAKVFSI--FEELGISVDVVATSEVSVSLTLDPSKLWSRELIQQASELDHVVEELEKIAV
                421                                                       480

SEQ ID NO:06    VRLLQQRAIISLIGNVEQSSLILEKTGRVLRKSGVNVQMISQGASKVNMSLIVHDSDAKA
SEQ ID NO:08    VRLLQQRAIISLIGNVEQSSLILEKTGRVLRKSGVNVQMISQGASKVNMSLIVHDSDAKA
SEQ ID NO:17    VNLLQNRSIISLIGNVQRSSLILERLSRVLRTLGVTVQMISQGASKVNISLVVNDSEAEQ
                481                                                       540

SEQ ID NO:06    LVEALHQAFFEDDVLSQVEAENLL------VG
SEQ ID NO:08    LVEALHQAFFEDDVLSQVEAENLL------VG
SEQ ID NO:17    CVRALHSAFFESE-LSELEMDYKNGNGSVDELS
                541                            573
```

SEQUENCE LISTING

<160> NUMBER OF SEQ ID NOS: 28

<210> SEQ ID NO 1
<211> LENGTH: 565
<212> TYPE: DNA
<213> ORGANISM: Zea mays
<220> FEATURE:
<221> NAME/KEY: unsure
<222> LOCATION: (127)
<223> OTHER INFORMATION: n=a,c,g or t

<400> SEQUENCE: 1

```
gcacgaggtt gaagagcttg agaaaatagc aattgttcgt ctacttcagc agagggcgat      60
aatttcactt atcggaaatg tggagcaatc gtctctcata ctagaaaaga cgggacgtgt     120
```

| | |
|---|---|
| gctgagngaa agtggggtta atgttcagat gatctcgcaa ggagcgtcaa aggttaacat | 180 |
| gtcgctgata gtccatgata gcgatgcaaa ggcactcgta gaagcccttc atcaggcgtt | 240 |
| ctttgaagac gatgtcctat cacaagtcga agcggagaac ctactcgtgg gctgatcaac | 300 |
| gtaggctttg ctgggtccag gcgtgttatc tgttatagat tcccactcgc ctccatgaac | 360 |
| ggcatgggca ttggatcatt gatcatgttt tgcttgaaac aagtatgtct tccaggttct | 420 |
| cagccaatga ctgcaaaact gtgtttctgt tttagaactg tttgcagaca ccagtgagct | 480 |
| gcgagcaccg attgtcaaca agatggcaag cctgtgatat aattccaact gtctctaatc | 540 |
| aatatatata ataaacatta tcaat | 565 |

<210> SEQ ID NO 2
<211> LENGTH: 97
<212> TYPE: PRT
<213> ORGANISM: Zea mays
<220> FEATURE:
<221> NAME/KEY: unsure
<222> LOCATION: (42)
<223> OTHER INFORMATION: Xaa=any amino acid

<400> SEQUENCE: 2

His Glu Val Glu Glu Leu Glu Lys Ile Ala Ile Val Arg Leu Leu Gln
 1               5                  10                  15

Gln Arg Ala Ile Ile Ser Leu Ile Gly Asn Val Glu Gln Ser Ser Leu
            20                  25                  30

Ile Leu Glu Lys Thr Gly Arg Val Leu Xaa Glu Ser Gly Val Asn Val
        35                  40                  45

Gln Met Ile Ser Gln Gly Ala Ser Lys Val Asn Met Ser Leu Ile Val
    50                  55                  60

His Asp Ser Asp Ala Lys Ala Leu Val Glu Ala Leu His Gln Ala Phe
65                  70                  75                  80

Phe Glu Asp Asp Val Leu Ser Gln Val Glu Ala Glu Asn Leu Leu Val
                85                  90                  95

Gly

<210> SEQ ID NO 3
<211> LENGTH: 513
<212> TYPE: DNA
<213> ORGANISM: Zea mays
<220> FEATURE:
<221> NAME/KEY: unsure
<222> LOCATION: (474)
<223> OTHER INFORMATION: n=a,c,g or t

<400> SEQUENCE: 3

| | |
|---|---|
| acagagcagg aggactcaga aatggcaatc ccagtgcgat cggctgccgc gccccgccgc | 60 |
| ctcgttccgt cgatacctcc ggcgagctct ggacatgttc gaggactggc gtgcttcggt | 120 |
| acccgaaccg ggcctcgcgg tgcaagaggg ttgtcaatgg tggtcgccga ctccaccagc | 180 |
| cgtcgggcca agcaagcgga cggcggggac ggcgtccttg ggcgcctgt tctcggaggg | 240 |
| ctcgggatgg agggattggg ggatcagctc agcgtggtga tgaagttcgg ggggtcctcg | 300 |
| gtgtcgtcgg ccgcgaggat ggctgaggtg gccggcctca tcctgacgtt ccccgaggag | 360 |
| cgccccgtcg tcgttctctc tgccatgggg aaaaccacca caaccttct ccttgctggg | 420 |
| agaaaaggca ataaggtgtg gagttatcat gttttctgaa atccgaagaa tggnatatgg | 480 |
| tcaaaaagcc taaatatca aagtatccca act | 513 |

```
<210> SEQ ID NO 4
<211> LENGTH: 152
<212> TYPE: PRT
<213> ORGANISM: Zea mays

<400> SEQUENCE: 4

Thr Glu Gln Glu Asp Ser Glu Met Ala Ile Pro Val Arg Ser Ala Ala
 1               5                  10                  15

Ala Pro Arg Arg Leu Val Pro Ser Ile Pro Pro Ala Ser Ser Gly His
             20                  25                  30

Val Arg Gly Leu Ala Cys Phe Gly Thr Arg Thr Gly Pro Arg Gly Ala
         35                  40                  45

Arg Gly Leu Ser Met Val Val Ala Asp Ser Thr Ser Arg Arg Ala Lys
     50                  55                  60

Gln Ala Asp Gly Gly Asp Gly Val Leu Gly Ala Pro Val Leu Gly Gly
 65                  70                  75                  80

Leu Gly Met Glu Gly Leu Gly Asp Gln Leu Ser Val Val Met Lys Phe
                 85                  90                  95

Gly Gly Ser Ser Val Ser Ser Ala Ala Arg Met Ala Glu Val Ala Gly
            100                 105                 110

Leu Ile Leu Thr Phe Pro Glu Arg Pro Val Val Leu Ser Ala
        115                 120                 125

Met Gly Lys Thr Thr Asn Asn Leu Leu Leu Ala Gly Arg Lys Gly Asn
    130                 135                 140

Lys Val Trp Ser Tyr His Val Phe
145                 150

<210> SEQ ID NO 5
<211> LENGTH: 1985
<212> TYPE: DNA
<213> ORGANISM: Zea mays
<220> FEATURE:
<221> NAME/KEY: unsure
<222> LOCATION: (532)
<223> OTHER INFORMATION: n=a,c,g or t
<220> FEATURE:
<221> NAME/KEY: unsure
<222> LOCATION: (1180)
<223> OTHER INFORMATION: n=a,c,g or t

<400> SEQUENCE: 5
gcaccagaca gagcaggagg actcagaaat ggcaatccca gtgcgatcgg ctgccgcgcc      60
ccgccgcctc gttccgtcga tacctccggc gagctctgga catgttcgag gactggcgtg     120
cttcggtacc cgaaccgggc ctcgcggtgc aagagggttg tcaatggtgg tcgccgactc     180
caccagccgt cgggccaagc aagcggacgg cgggacggc gtccttgggg cgcctgttct      240
cggagggctc gggatggagg gattggggga tcagctcagc gtggtgatga agttcggggg     300
gtcctcggtg tcgtcggccg cgaggatggc tgaggtggcc ggcctcatcc tgacgttccc     360
cgaggagcgc cccgtcgtcg ttctctctgc catggggaaa accaccaaca accttctcct     420
tgctggagag aaggcagtag ggtgtggagt tatccatgtt tctgaaatcg aagagtggaa     480
tatggtcaaa agcctacata tcaagacggt ggatgaactt ggacttccaa gnatctgtaa     540 tacaagccctt tatgaactgg agcaactatt gaaaggtatc gctatgatga aagagctgac     600
gcctaggacc agtgactacc ttgtttcatt tggagaatgc atgtccacca ggattttttc     660
tgcttatttg aacaaaattc gtgtcaaggc acggcagtat gacgcatttg atattggttt     720
cattacaact gatgaatttg gtaatgcgga tatcttagaa gcaacctatc ctgctgttgc     780
```

-continued

```
gaagagactt catggggact ggatacagga tccagcgata cctgttgtta ctgggttcct      840
tgggaagggc tggaaatctg gtgctgtaac tactttaggc cgaggtggta gtgacttgac      900
tgctacaacc attggtaaag ccttgggact gagagaaatt caggtatgga agatgttga       960 tggtgtactt acttgtgatc caaatatcta cccacatgca aagactgttc catacttaac    1020
atttgaagag gccacagaac ttgcttattt tggtgctcag gttttgcatc cacaatcgat    1080
gagacctgct agagaaggtg atattccagt tagggttaag aattcataca ccctaaagc     1140 tccaggcacc cttattacca gacaaagaga catggataan ggtctggttg tactaactag    1200
catagtgctc aagtcaaatg tcactatgtt ggacattgtg agcactcgga tgcttggtca    1260
gtatggtttt ctggcaaggg tatcaggtat ttgctatatt aagatctat gtatatctgt     1320 ggattgtgtt gctaccagtg aagttagtgt ttctgtgtca cttgatccat caaagatctg    1380
gagtagggaa ctgatacagc aggcaagtga acttgaccat gtagttgaag agcttgagaa    1440
aatagcaatt gttcgtctac ttcagcagag ggcgataatt tcacttatcg gaaatgtgga    1500
gcaatcgtct ctgatactag aaaagacggg acgtgtgctg aggaaaagtg gggttaatgt    1560
tcagatgatc tcgcaaggag cgtcaaaggt taacatgtcg ctgatagtcc atgatagcga    1620
tgcaaaggca ctcgtagaag cccttcatca ggcgttcttt gaagacgatg tcctatcaca    1680
agtcgaagcg gagaacctac tcgtgggctg atcaacgtag gctttgctgg gtccaggcgt    1740
gttatctgtt atagattccc actcgcctcc atgaacggca tgggcattgg atcattgatc    1800
atgttttgct tgaaacaagt atgtcttcca ggttctcagc caatgactgc aaaactgtgt    1860
ttctgtttta gaactgtttg cagacaccag tgagctgcga gcaccgattg tcaacaagat    1920
ggcaagcctg tgatataatt ccaactgtct ctaatcaata tatataataa acattatcaa    1980
tatct                                                                 1985
```

<210> SEQ ID NO 6
<211> LENGTH: 560
<212> TYPE: PRT
<213> ORGANISM: Zea mays
<220> FEATURE:
<221> NAME/KEY: UNSURE
<222> LOCATION: (168)
<223> OTHER INFORMATION: Xaa=any amino acid
<220> FEATURE:
<221> NAME/KEY: UNSURE
<222> LOCATION: (384)
<223> OTHER INFORMATION: Xaa=any amino acid

<400> SEQUENCE: 6

```
Met Ala Ile Pro Val Arg Ser Ala Ala Pro Arg Arg Leu Val Pro
  1               5                  10                  15

Ser Ile Pro Pro Ala Ser Ser Gly His Val Arg Gly Leu Ala Cys Phe
                 20                  25                  30

Gly Thr Arg Thr Gly Pro Arg Gly Ala Arg Gly Leu Ser Met Val Val
            35                  40                  45

Ala Asp Ser Thr Ser Arg Arg Ala Lys Gln Ala Asp Gly Gly Asp Gly
        50                  55                  60

Val Leu Gly Ala Pro Val Leu Gly Gly Leu Gly Met Glu Gly Leu Gly
 65                  70                  75                  80

Asp Gln Leu Ser Val Val Met Lys Phe Gly Gly Ser Ser Val Ser Ser
                 85                  90                  95

Ala Ala Arg Met Ala Glu Val Ala Gly Leu Ile Leu Thr Phe Pro Glu
                100                 105                 110
```

```
Glu Arg Pro Val Val Val Leu Ser Ala Met Gly Lys Thr Thr Asn Asn
            115                 120                 125
Leu Leu Leu Ala Gly Glu Lys Ala Val Gly Cys Gly Val Ile His Val
130                 135                 140
Ser Glu Ile Glu Glu Trp Asn Met Val Lys Ser Leu His Ile Lys Thr
145                 150                 155                 160
Val Asp Glu Leu Gly Leu Pro Xaa Ile Cys Asn Thr Ser Leu Tyr Glu
                165                 170                 175
Leu Glu Gln Leu Leu Lys Gly Ile Ala Met Met Lys Glu Leu Thr Pro
            180                 185                 190
Arg Thr Ser Asp Tyr Leu Val Ser Phe Gly Glu Cys Met Ser Thr Arg
        195                 200                 205
Ile Phe Ser Ala Tyr Leu Asn Lys Ile Arg Val Lys Ala Arg Gln Tyr
210                 215                 220
Asp Ala Phe Asp Ile Gly Phe Ile Thr Thr Asp Glu Phe Gly Asn Ala
225                 230                 235                 240
Asp Ile Leu Glu Ala Thr Tyr Pro Ala Val Ala Lys Arg Leu His Gly
                245                 250                 255
Asp Trp Ile Gln Asp Pro Ala Ile Pro Val Val Thr Gly Phe Leu Gly
            260                 265                 270
Lys Gly Trp Lys Ser Gly Ala Val Thr Thr Leu Gly Arg Gly Gly Ser
        275                 280                 285
Asp Leu Thr Ala Thr Thr Ile Gly Lys Ala Leu Gly Leu Arg Glu Ile
290                 295                 300
Gln Val Trp Lys Asp Val Asp Gly Val Leu Thr Cys Asp Pro Asn Ile
305                 310                 315                 320
Tyr Pro His Ala Lys Thr Val Pro Tyr Leu Thr Phe Glu Glu Ala Thr
                325                 330                 335
Glu Leu Ala Tyr Phe Gly Ala Gln Val Leu His Pro Gln Ser Met Arg
            340                 345                 350
Pro Ala Arg Glu Gly Asp Ile Pro Val Arg Val Lys Asn Ser Tyr Asn
        355                 360                 365
Pro Lys Ala Pro Gly Thr Leu Ile Thr Arg Gln Arg Asp Met Asp Xaa
370                 375                 380
Gly Leu Val Val Leu Thr Ser Ile Val Leu Lys Ser Asn Val Thr Met
385                 390                 395                 400
Leu Asp Ile Val Ser Thr Arg Met Leu Gly Gln Tyr Gly Phe Leu Ala
                405                 410                 415
Arg Val Ser Gly Ile Cys Tyr Ile Glu Asp Leu Cys Ile Ser Val Asp
            420                 425                 430
Cys Val Ala Thr Ser Glu Val Ser Val Ser Val Ser Leu Asp Pro Ser
        435                 440                 445
Lys Ile Trp Ser Arg Glu Leu Ile Gln Gln Ala Ser Glu Leu Asp His
450                 455                 460
Val Val Glu Glu Leu Glu Lys Ile Ala Ile Val Arg Leu Leu Gln Gln
465                 470                 475                 480
Arg Ala Ile Ile Ser Leu Ile Gly Asn Val Glu Gln Ser Ser Leu Ile
                485                 490                 495
Leu Glu Lys Thr Gly Arg Val Leu Arg Lys Ser Gly Val Asn Val Gln
            500                 505                 510
Met Ile Ser Gln Gly Ala Ser Lys Val Asn Met Ser Leu Ile Val His
        515                 520                 525
Asp Ser Asp Ala Lys Ala Leu Val Glu Ala Leu His Gln Ala Phe Phe
```

|  530  |  | | | 535 | | | | | 540 | | |
|---|---|---|---|---|---|---|---|---|---|---|---|
| Glu | Asp | Asp | Val | Leu | Ser | Gln | Val | Glu | Ala | Glu | |
| 545 | | | | | 550 | | | | 555 | | |
| Asn | Leu | Leu | Val | Gly | | | | | | | |
| | | | | 560 | | | | | | | |

<210> SEQ ID NO 7
<211> LENGTH: 1953
<212> TYPE: DNA
<213> ORGANISM: Zea mays

<400> SEQUENCE: 7

```
gagcaggagg actcagaaat ggcaatccca gtgcgatcgg ctgccgcgcc ccgccgcctc      60
gttccgtcga tacctccggc gagctctgga catgttcgag gactggcgtg cttcggtacc     120
cgaaccgggc ctcgcggtgc aagagggttg tcaatggtgg tcgccgactc caccagccgt     180
cgggccaagc aagcggacgg cggggacggc gtccttgggg cgcctgttct cggagggctc     240
gggatggagg gattggggga tcagctcagc gtggtgatga gttcggggg gtcctcggtg      300
tcgtcggccg cgaggatggc tgaggtggcc ggcctcatcc tgacgttccc cgaggagcgc     360
cccgtcgtcg ttctctctgc catggggaaa accaccaaca accttctcct tgctggagag     420
aaggcagtag ggtgtggagt tatccatgtt tctgaaatcg aagagtggaa tatggtcaaa     480
agcctacata tcaagacggt ggatgaactt ggacttccaa gatctgtaat acaagacatg     540
ctagatgaac tggagcaact attgaaaggt atcgctatga tgaaagagct gacgcctagg     600
accagtgact accttgtttc atttggagaa tgcatgtcca ccaggatttt ttctgcttat     660
tgaacaaaa ttcgtgtcaa ggcacggcag tatgacgcat ttgatattgg tttcattaca     720
actgatgaat ttggtaatgc ggatatctta gaagcaacct atcctgctgt tgcgaagaga     780
cttcatgggg actggataca ggatccagcg atacctgttg ttactgggtt ccttgggaag     840
ggctggaaat ctggtgctgt aactacttta ggccgaggtg gtagtgactt gactgctaca     900
accattggta aagcctttggg actgagagaa attcaggtat ggaaagatgt tgatggtgta     960
cttacttgtg atccaaatat ctacccacat gcaaagactg ttccatactt aacatttgaa    1020
gaggccacag aacttgctta ttttggtgct caggttttgc atccacaatc gatgagacct    1080
gctagagaag gtgatattcc agttagggtt aagaattcat acaaccctaa agctccaggc    1140
acccttatta ccagacaaag agacatggat aaggttgtac taactagcat agtgctcaag    1200
tcaaatgtca ctatgttgga cattgtgagc actcggatgc ttggtcagta tggttttctg    1260
gcaagggtat ttgctatatt tgaagatcta tgtatatctg tggattgtgt tgctaccagt    1320
gaagttagtg tttctgtgtc acttgatcca tcaaagatct ggagtaggga actgatacag    1380
caggaacttg accatgtagt tgaagagctt gagaaaatag caattgttcg tctacttcag    1440
cagagggcga taatttcact tatcggaaat gtggagcaat cgtctctcat actagaaaag    1500
acggacgtg tgctgaggaa aagtgggggtt aatgttcaga tgatctcgca aggagcgtca    1560
aaggttaaca tgtcgctgat agtccatgat agcgatgcaa aggcactcgt agaagccctt    1620
catcaggcgt tctttgaaga cgatgtccta tcacaagtcg aagcggagaa cctactcgtg    1680
ggctgatcaa cgtaggcttt gctgggtcca ggcgtgttat ctgttataga ttcccactcg    1740
cctccatgaa cggcatgggc attggatcat tgatcatgtt ttgcttgaaa caagtatgtc    1800
ttccaggttc tcagccaatg actgcaaaac tgtgtttctg ttttagaact gtttgcagac    1860
accagtgagc tgcagcacc gattgtcaac aagatggcaa gcctgtgata taattccaac    1920
tgtctctaat caatatatat aataaacatt atc                                 1953
```

```
<210> SEQ ID NO 8
<211> LENGTH: 555
<212> TYPE: PRT
<213> ORGANISM: Zea mays

<400> SEQUENCE: 8

Met Ala Ile Pro Val Arg Ser Ala Ala Pro Arg Arg Leu Val Pro
  1               5                  10                  15

Ser Ile Pro Pro Ala Ser Ser Gly His Val Arg Gly Leu Ala Cys Phe
                 20                  25                  30

Gly Thr Arg Thr Gly Pro Arg Gly Ala Arg Gly Leu Ser Met Val Val
             35                  40                  45

Ala Asp Ser Thr Ser Arg Arg Ala Lys Gln Ala Asp Gly Gly Asp Gly
 50                  55                  60

Val Leu Gly Ala Pro Val Leu Gly Gly Leu Gly Met Glu Gly Leu Gly
 65                  70                  75                  80

Asp Gln Leu Ser Val Val Met Lys Phe Gly Ser Ser Val Ser Ser
                 85                  90                  95

Ala Ala Arg Met Ala Glu Val Ala Gly Leu Ile Leu Thr Phe Pro Glu
                100                 105                 110

Glu Arg Pro Val Val Val Leu Ser Ala Met Gly Lys Thr Thr Asn Asn
            115                 120                 125

Leu Leu Leu Ala Gly Glu Lys Ala Val Gly Cys Gly Val Ile His Val
        130                 135                 140

Ser Glu Ile Glu Glu Trp Asn Met Val Lys Ser Leu His Ile Lys Thr
145                 150                 155                 160

Val Asp Glu Leu Gly Leu Pro Arg Ser Val Ile Gln Asp Met Leu Asp
                165                 170                 175

Glu Leu Glu Gln Leu Leu Lys Gly Ile Ala Met Met Lys Glu Leu Thr
            180                 185                 190

Pro Arg Thr Ser Asp Tyr Leu Val Ser Phe Gly Glu Cys Met Ser Thr
        195                 200                 205

Arg Ile Phe Ser Ala Tyr Leu Asn Lys Ile Arg Val Lys Ala Arg Gln
210                 215                 220

Tyr Asp Ala Phe Asp Ile Gly Phe Ile Thr Thr Asp Glu Phe Gly Asn
225                 230                 235                 240

Ala Asp Ile Leu Glu Ala Thr Tyr Pro Ala Val Ala Lys Arg Leu His
                245                 250                 255

Gly Asp Trp Ile Gln Asp Pro Ala Ile Pro Val Val Thr Gly Phe Leu
            260                 265                 270

Gly Lys Gly Trp Lys Ser Gly Ala Val Thr Thr Leu Gly Arg Gly Gly
        275                 280                 285

Ser Asp Leu Thr Ala Thr Thr Ile Gly Lys Ala Leu Gly Leu Arg Glu
290                 295                 300

Ile Gln Val Trp Lys Asp Val Asp Gly Val Leu Thr Cys Asp Pro Asn
305                 310                 315                 320

Ile Tyr Pro His Ala Lys Thr Val Pro Tyr Leu Thr Phe Glu Glu Ala
                325                 330                 335

Thr Glu Leu Ala Tyr Phe Gly Ala Gln Val Leu His Pro Gln Ser Met
            340                 345                 350

Arg Pro Ala Arg Glu Gly Asp Ile Pro Val Arg Val Lys Asn Ser Tyr
        355                 360                 365

Asn Pro Lys Ala Pro Gly Thr Leu Ile Thr Arg Gln Arg Asp Met Asp
370                 375                 380
```

```
Lys Val Val Leu Thr Ser Ile Val Leu Lys Ser Asn Val Thr Met Leu
385                 390                 395                 400

Asp Ile Val Ser Thr Arg Met Leu Gly Gln Tyr Gly Phe Leu Ala Arg
            405                 410                 415

Val Phe Ala Ile Phe Glu Asp Leu Cys Ile Ser Val Asp Cys Val Ala
                420                 425                 430

Thr Ser Glu Val Ser Val Ser Val Ser Leu Asp Pro Ser Lys Ile Trp
        435                 440                 445

Ser Arg Glu Leu Ile Gln Gln Glu Leu Asp His Val Val Glu Glu Leu
    450                 455                 460

Glu Lys Ile Ala Ile Val Arg Leu Leu Gln Gln Arg Ala Ile Ile Ser
465                 470                 475                 480

Leu Ile Gly Asn Val Glu Gln Ser Ser Leu Ile Leu Glu Lys Thr Gly
                485                 490                 495

Arg Val Leu Arg Lys Ser Gly Val Asn Val Gln Met Ile Ser Gln Gly
            500                 505                 510

Ala Ser Lys Val Asn Met Ser Leu Ile Val His Asp Ser Asp Ala Lys
        515                 520                 525

Ala Leu Val Glu Ala Leu His Gln Ala Phe Phe Glu Asp Asp Val Leu
    530                 535                 540

Ser Gln Val Glu Ala Glu Asn Leu Leu Val Gly
545                 550                 555

<210> SEQ ID NO 9
<211> LENGTH: 455
<212> TYPE: DNA
<213> ORGANISM: Oryza sativa
<220> FEATURE:
<221> NAME/KEY: unsure
<222> LOCATION: (366)
<223> OTHER INFORMATION: n=a,c,g or t
<220> FEATURE:
<221> NAME/KEY: unsure
<222> LOCATION: (394)
<223> OTHER INFORMATION: n=a,c,g or t
<220> FEATURE:
<221> NAME/KEY: unsure
<222> LOCATION: (406)
<223> OTHER INFORMATION: n=a,c,g or t
<220> FEATURE:
<221> NAME/KEY: unsure
<222> LOCATION: (414)
<223> OTHER INFORMATION: n=a,c,g or t
<220> FEATURE:
<221> NAME/KEY: unsure
<222> LOCATION: (425)
<223> OTHER INFORMATION: n=a,c,g or t
<220> FEATURE:
<221> NAME/KEY: unsure
<222> LOCATION: (431)
<223> OTHER INFORMATION: n=a,c,g or t
<220> FEATURE:
<221> NAME/KEY: unsure
<222> LOCATION: (455)
<223> OTHER INFORMATION: n=a,c,g or t

<400> SEQUENCE: 9
caacgctttg ccaatggtgg tagcagtcaa gtcgctgcca cctctgccta aagtggtgac      60
agcacatgat ttccatcctt ttccaaggaa accagtaact ataggaatag cagggtcgtc     120
aatccaatca ccctgtaacc tctttgcaac agcaggatat gtcgcttcaa gaatgtccgc     180
atttgtgaaa tcatcagtag ttataaagcc aatatcaaat gcatcatact gccgagcctt     240
tttcccaagt ttattcaaat atgcaagcaa atattcttgt agacatgcat tcaccgaagg     300
```

```
aaacaaggta atcccgtgtc ctaaggagtt aagttctttc aatcaatagc aacaccctta    360
aagaangttg gttccaattc cttccaaata aaanccttga aacaantccg gatnctaatc    420
ccaantccca nagcctcatc aaattagtcc ctaan                              455

<210> SEQ ID NO 10
<211> LENGTH: 114
<212> TYPE: PRT
<213> ORGANISM: Oryza sativa

<400> SEQUENCE: 10

Leu Lys Glu Leu Asn Ser Leu Gly His Gly Ile Thr Leu Phe Pro Ser
  1               5                  10                  15

Val Asn Ala Cys Leu Gln Glu Tyr Leu Leu Ala Tyr Leu Asn Lys Leu
             20                  25                  30

Gly Lys Lys Ala Arg Gln Tyr Asp Ala Phe Asp Ile Gly Phe Ile Thr
         35                  40                  45

Thr Asp Asp Phe Thr Asn Ala Asp Ile Leu Glu Ala Thr Tyr Pro Ala
     50                  55                  60

Val Ala Lys Arg Leu Gln Gly Asp Trp Ile Asp Asp Pro Ala Ile Pro
 65                  70                  75                  80

Ile Val Thr Gly Phe Leu Gly Lys Gly Trp Lys Ser Cys Ala Val Thr
                 85                  90                  95

Thr Leu Gly Arg Gly Gly Ser Asp Leu Thr Ala Thr Thr Ile Gly Lys
            100                 105                 110

Ala Leu

<210> SEQ ID NO 11
<211> LENGTH: 847
<212> TYPE: DNA
<213> ORGANISM: Oryza sativa

<400> SEQUENCE: 11 ctcccccag  ggtggggagg gagcagcagt atctcgcgtg cgcggcggcg gcgaggccgg     60
gagggaggtg ttcgaggagg aggggattgg tggtgcggtg ccagagcggg gcggcggcgg    120
ttgtcctcaa caaggacgac gcggcgtcgg tggccgccgc cgccgcctcc tccgcgacgg    180
ggttcaccgt cgccatgaag ttcggcgggt cgtcggtggc gtcggcggag cggatgcggg    240
aggtggccga tctcatactc agcttccccg aggagactcc cgttgttgtt ctctccgcca    300
tggggaagac caccaataac ctcctcctgg ccggagagaa ggctgtcagc tgcggcgccc    360
cgaaggcgtc tgaaattccc gagctcgcag ttatcaagga gctccatgtt aggactattg    420
atgagcttgg attggataga tcgattgttt caggtttatt ggaagaattg gaacaacttc    480
ttaagggtgt tgctatgatg aaagaactaa ctcctaggac acgggattac cttgtttcct    540
tcggtgaatg catgtctaca agaatatttg ctgcatattt gaataaactt gggaaaaagg    600
ctcggcagta tgatgcattt gatattggct ttataactac tgatgatttc acaaatgcgg    660
acattcttga agcgacatat cctgctgttg caaagaggtt acagggtgat tggattgacg    720
accctgctat tcctatagtt actggttttc ttggaaaagg atggaaatca tgtgctgtca    780
ccactttagg cagaggtggc agcgacttga ctgctaccac cattggcaaa gcgttgcgga    840
cgcgtgg                                                             847

<210> SEQ ID NO 12
<211> LENGTH: 281
```

```
<212> TYPE: PRT
<213> ORGANISM: Oryza sativa

<400> SEQUENCE: 12

Pro Pro Arg Val Gly Arg Glu Gln Gln Tyr Leu Ala Cys Ala Ala Ala
 1               5                  10                  15

Ala Arg Pro Gly Gly Arg Cys Ser Arg Arg Gly Leu Val Val Arg
             20                  25                  30

Cys Gln Ser Gly Ala Ala Val Val Leu Asn Lys Asp Asp Ala Ala
         35                  40                  45

Ser Val Ala Ala Ala Ala Ser Ser Ala Thr Gly Phe Thr Val Ala
 50                  55                  60

Met Lys Phe Gly Gly Ser Ser Val Ala Ser Ala Glu Arg Met Arg Glu
 65                  70                  75                  80

Val Ala Asp Leu Ile Leu Ser Phe Pro Glu Glu Thr Pro Val Val Val
                 85                  90                  95

Leu Ser Ala Met Gly Lys Thr Thr Asn Asn Leu Leu Leu Ala Gly Glu
                100                 105                 110

Lys Ala Val Ser Cys Gly Ala Pro Lys Ala Ser Glu Ile Pro Glu Leu
                115                 120                 125

Ala Val Ile Lys Glu Leu His Val Arg Thr Ile Asp Glu Leu Gly Leu
130                 135                 140

Asp Arg Ser Ile Val Ser Gly Leu Leu Glu Glu Leu Glu Gln Leu Leu
145                 150                 155                 160

Lys Gly Val Ala Met Met Lys Glu Leu Thr Pro Arg Thr Arg Asp Tyr
                165                 170                 175

Leu Val Ser Phe Gly Glu Cys Met Ser Thr Arg Ile Phe Ala Ala Tyr
                180                 185                 190

Leu Asn Lys Leu Gly Lys Lys Ala Arg Gln Tyr Asp Ala Phe Asp Ile
                195                 200                 205

Gly Phe Ile Thr Thr Asp Asp Phe Thr Asn Ala Asp Ile Leu Glu Ala
                210                 215                 220

Thr Tyr Pro Ala Val Ala Lys Arg Leu Gln Gly Asp Trp Ile Asp Asp
225                 230                 235                 240

Pro Ala Ile Pro Ile Val Thr Gly Phe Leu Gly Lys Gly Trp Lys Ser
                245                 250                 255

Cys Ala Val Thr Thr Leu Gly Arg Gly Gly Ser Asp Leu Thr Ala Thr
                260                 265                 270

Thr Ile Gly Lys Ala Leu Arg Thr Arg
                275                 280

<210> SEQ ID NO 13
<211> LENGTH: 646
<212> TYPE: DNA
<213> ORGANISM: Triticum aestivum
<220> FEATURE:
<221> NAME/KEY: unsure
<222> LOCATION: (289)
<223> OTHER INFORMATION: n=a,c,g or t
<220> FEATURE:
<221> NAME/KEY: unsure
<222> LOCATION: (329)
<223> OTHER INFORMATION: n=a,c,g or t
<220> FEATURE:
<221> NAME/KEY: unsure
<222> LOCATION: (393)
<223> OTHER INFORMATION: n=a,c,g or t
<220> FEATURE:
<221> NAME/KEY: unsure
<222> LOCATION: (435)
```

```
<223> OTHER INFORMATION: n=a,c,g or t
<220> FEATURE:
<221> NAME/KEY: unsure
<222> LOCATION: (551)
<223> OTHER INFORMATION: n=a,c,g or t
<220> FEATURE:
<221> NAME/KEY: unsure
<222> LOCATION: (582)
<223> OTHER INFORMATION: n=a,c,g or t
<220> FEATURE:
<221> NAME/KEY: unsure
<222> LOCATION: (616)
<223> OTHER INFORMATION: n=a,c,g or t
<220> FEATURE:
<221> NAME/KEY: unsure
<222> LOCATION: (626)
<223> OTHER INFORMATION: n=a,c,g or t
<220> FEATURE:
<221> NAME/KEY: unsure
<222> LOCATION: (632)
<223> OTHER INFORMATION: n=a,c,g or t
<220> FEATURE:
<221> NAME/KEY: unsure
<222> LOCATION: (637)
<223> OTHER INFORMATION: n=a,c,g or t
<220> FEATURE:
<221> NAME/KEY: unsure
<222> LOCATION: (640)
<223> OTHER INFORMATION: n=a,c,g or t

<400> SEQUENCE: 13
ggcggtgagc tgcggcgccc ccaaggcgtc ggaaatctac gagctcgccg tcatcaagga      60
gctccatctc aggaccatcg atgagcttgg cctagatagc tccattgttt caggtttttt     120
ggacgagttg gagcaactgc tcaagggtgt tgctatgatg aaagagctga ctcttaggac     180
acgagattac cttgtttcct ttggtgaatg catgtctaca agaatatttt ctgcatattt     240
gaataaacta gggaagaagg cacgacagta tgatgctttt gatcttggnt ttataaccac     300
tggacgattt ccacaaatgc cgatatccnc gaacaactta tcctgctgtt gcaaagagct     360
acatgggaat tggttgatga ccctgctatc ccnatatgac ggttcccttg ggaagggatg     420
gaacttgtgc ggcanaactt aggaaggggc ggaatgactt gacggcacaa ccatgggaaa     480
cctggggtta agaaaatcag gttggaagat gtaacggttt tgactgtgat caatattatc     540
aaaccggaca ntaccactta ctttgtaggg accgaacttc tnntttggaa agtttgacca     600
tcatcacacc aggagngacc cattcntaaa cnaaacntcn cccgga                    646

<210> SEQ ID NO 14
<211> LENGTH: 146
<212> TYPE: PRT
<213> ORGANISM: Triticum aestivum
<220> FEATURE:
<221> NAME/KEY: UNSURE
<222> LOCATION: (110)
<223> OTHER INFORMATION: Xaa=any amino acid
<220> FEATURE:
<221> NAME/KEY: UNSURE
<222> LOCATION: (131)
<223> OTHER INFORMATION: Xaa=any amino acid
<220> FEATURE:
<221> NAME/KEY: UNSURE
<222> LOCATION: (145)
<223> OTHER INFORMATION: Xaa=any amino acid

<400> SEQUENCE: 14

Ala Val Ser Cys Gly Ala Pro Lys Ala Ser Glu Ile Tyr Glu Leu Ala
 1               5                  10                  15

Val Ile Lys Glu Leu His Leu Arg Thr Ile Asp Glu Leu Gly Leu Asp
            20                  25                  30
```

```
Ser Ser Ile Val Ser Gly Phe Leu Asp Glu Leu Glu Gln Leu Leu Lys
         35                  40                  45

Gly Val Ala Met Met Lys Glu Leu Thr Leu Arg Thr Arg Asp Tyr Leu
 50                  55                  60

Val Ser Phe Gly Glu Cys Met Ser Thr Arg Ile Phe Ser Ala Tyr Leu
 65                  70                  75                  80

Asn Lys Leu Gly Lys Lys Ala Arg Gln Tyr Asp Ala Phe Asp Leu Gly
                 85                  90                  95

Phe Ile Thr Thr Gly Arg Phe Pro Gln Met Pro Ile Ser Xaa Asn Asn
                100                 105                 110

Leu Ser Cys Cys Cys Lys Glu Leu His Gly Asn Trp Leu Met Thr Leu
            115                 120                 125

Leu Ser Xaa Tyr Asp Gly Ser Leu Gly Lys Gly Trp Asn Leu Cys Gly
            130                 135                 140

Xaa Thr
145

<210> SEQ ID NO 15
<211> LENGTH: 1658
<212> TYPE: DNA
<213> ORGANISM: Triticum aestivum

<400> SEQUENCE: 15
ttcggcacga gggcggtgag ctgcggcgcc cccaaggcgt cggaaatcta cgagctcgcc      60
gtcatcaagg agctccatct caggaccatc gatgagcttg ccctagatag ctccattgtt     120
tcaggttttt tggacgagtt ggagcaactg ctcaagggtg ttgctatgat gaaagagctg     180
actcttagga cacgagatta ccttgtttcc tttggtgaat gcatgtctac aagaatattt     240
tctgcatatt tgaataaact agggaagaag gcacgacagt atgatgcttt tgatcttggc     300
tttataacca ctgacgattt cacaaatgcc gatattctcg aagcaactta tcctgctgtt     360
gcaaagaggc tacatggaga ttggattgat gaccctgcta ttcctatagt gactggtttc     420
cttgggaagg gatggaaatc ttgtgcggtc acaacgttag aaggggcgg cagtgacttg      480 accgctacaa ccattggcaa agccttgggg ttaagagaaa ttcaggtttg aaggatgta      540 gacggtgtgt tgacgtgtga tccaaatatt tatgcaaacg cggtaccagt accctacttg     600
acttttgatg aggcagctga acttgcttat tttggtgcac aggttttgca tccccaatcc     660
atgcgaccag ccaggaagg tggtatccca gttcgagtga agaactcata taaccgtcat      720
gcacctggca ctgtgatcac taaaacaaga gatatgcgca agagcatatt aaccagcatt     780
gtcctgaaat caaatattac catgctggat atagtgagca aaggatgct cggacagtat      840 ggctttctag caaaggtctt ctcaatattt gaagatttgg gtatctctgt tgattctgtg     900
gctactagtg aagtcagcat atcattgaca ctagatccat caaaactgtg gagtcgtgaa     960
ttgatccagc aggagcttga tcatgtagtt gaagagcttg aaaagattgc ggttgttcat    1020
ctcctacagc acagatcaat catttccctg atagggaatg tgcagagatc gtctctgatt    1080
cttgagaagg cgttcaatgt tctacgcaga aatggtgtta atgttcagat gatttcgcaa    1140
ggggcgtcca aggtgaacat ctccttggtg gtgaatgaca cgcgaggcgaa gcagtgcgtg    1200 caagccctcc actcggcatt ctttgagaac ggtttcttgt cagaagtaga ggaagcggac    1260
cttgcgcaga gagggctcc agtcctagta agctcgaatg gtgccatcaa cggaaactag     1320
tcgacgtcgc tttttctac ttccagcaac ggatgcgccg ttcttaggtt aagagggtga    1380
```

-continued

```
ttcgaccttg gattatttag gccacctgag ctgattcatt ggtgttgcac gagctatcat    1440
tggtgttgta agagtgagca gcatgattct tcgagtgcta gcatatggta gcccaatcaa    1500
tgtatgtgat tgtgaggcgt cctacttgct gaacttaacc attgtgagga gcccctatga    1560
acttatcctt gggtgtcttc taccaaatac taaatagtat gtgtgttgtt cctccaaaaa    1620
aaaaaaaaaa aaaaaaaaaa aaaaaaaaaa aaaaaaaa                            1658
```

<210> SEQ ID NO 16
<211> LENGTH: 439
<212> TYPE: PRT
<213> ORGANISM: Triticum aestivum

<400> SEQUENCE: 16

```
Phe Gly Thr Arg Ala Val Ser Cys Gly Ala Pro Lys Ala Ser Glu Ile
 1               5                  10                  15

Tyr Glu Leu Ala Val Ile Lys Glu Leu His Leu Arg Thr Ile Asp Glu
             20                  25                  30

Leu Gly Leu Asp Ser Ser Ile Val Ser Gly Phe Leu Asp Glu Leu Glu
         35                  40                  45

Gln Leu Leu Lys Gly Val Ala Met Met Lys Glu Leu Thr Leu Arg Thr
     50                  55                  60

Arg Asp Tyr Leu Val Ser Phe Gly Glu Cys Met Ser Thr Arg Ile Phe
 65                  70                  75                  80

Ser Ala Tyr Leu Asn Lys Leu Gly Lys Lys Ala Arg Gln Tyr Asp Ala
                 85                  90                  95

Phe Asp Leu Gly Phe Ile Thr Thr Asp Asp Phe Thr Asn Ala Asp Ile
            100                 105                 110

Leu Glu Ala Thr Tyr Pro Ala Val Ala Lys Arg Leu His Gly Asp Trp
        115                 120                 125

Ile Asp Asp Pro Ala Ile Pro Ile Val Thr Gly Phe Leu Gly Lys Gly
    130                 135                 140

Trp Lys Ser Cys Ala Val Thr Thr Leu Gly Arg Gly Gly Ser Asp Leu
145                 150                 155                 160

Thr Ala Thr Thr Ile Gly Lys Ala Leu Gly Leu Arg Glu Ile Gln Val
                165                 170                 175

Trp Lys Asp Val Asp Gly Val Leu Thr Cys Asp Pro Asn Ile Tyr Ala
            180                 185                 190

Asn Ala Val Pro Val Pro Tyr Leu Thr Phe Asp Glu Ala Ala Glu Leu
        195                 200                 205

Ala Tyr Phe Gly Ala Gln Val Leu His Pro Gln Ser Met Arg Pro Ala
    210                 215                 220

Arg Glu Gly Gly Ile Pro Val Arg Val Lys Asn Ser Tyr Asn Arg His
225                 230                 235                 240

Ala Pro Gly Thr Val Ile Thr Lys Thr Arg Asp Met Arg Lys Ser Ile
                245                 250                 255

Leu Thr Ser Ile Val Leu Lys Ser Asn Ile Thr Met Leu Asp Ile Val
            260                 265                 270

Ser Thr Arg Met Leu Gly Gln Tyr Gly Phe Leu Ala Lys Val Phe Ser
        275                 280                 285

Ile Phe Glu Asp Leu Gly Ile Ser Val Asp Ser Val Ala Thr Ser Glu
    290                 295                 300

Val Ser Ile Ser Leu Thr Leu Asp Pro Ser Lys Leu Trp Ser Arg Glu
305                 310                 315                 320

Leu Ile Gln Gln Glu Leu Asp His Val Val Glu Glu Leu Glu Lys Ile
```

-continued

```
                325                 330                 335

Ala Val Val His Leu Leu Gln His Arg Ser Ile Ile Ser Leu Ile Gly
        340                 345                 350

Asn Val Gln Arg Ser Ser Leu Ile Leu Glu Lys Ala Phe Asn Val Leu
        355                 360                 365

Arg Arg Asn Gly Val Asn Val Gln Met Ile Ser Gln Gly Ala Ser Lys
        370                 375                 380

Val Asn Ile Ser Leu Val Val Asn Asp Ser Glu Ala Lys Gln Cys Val
385                 390                 395                 400

Gln Ala Leu His Ser Ala Phe Phe Glu Asn Gly Phe Leu Ser Glu Val
                405                 410                 415

Glu Glu Ala Asp Leu Ala Gln Lys Arg Ala Pro Val Leu Val Ser Ser
                420                 425                 430

Asn Gly Ala Ile Asn Gly Asn
                435
```

<210> SEQ ID NO 17
<211> LENGTH: 564
<212> TYPE: PRT
<213> ORGANISM: Glycine max

<400> SEQUENCE: 17

```
Met Ala Ser Ala Leu Gln Gln Leu Gln Gly Val Gln Gly Lys Leu Ala
  1               5                  10                  15

Val Ser Met Ser Val Arg Arg Ser Leu His His Cys Lys Ser Gln Ile
                 20                  25                  30

Gly Phe Ala Ala Leu Gly Ala Pro Val Cys Ala Arg Arg Val Trp Gly
             35                  40                  45

Asn Arg Val Ala Phe Ser Val Thr Thr Cys Lys Ala Ser Thr Ser Asp
         50                  55                  60

Val Ile Glu Lys Asn Ala Thr Glu Asn Gly Met Val Ser Ser Glu Gly
 65                  70                  75                  80

Glu Thr Ser Phe Thr Cys Val Met Lys Phe Gly Gly Ser Ser Val Ala
                 85                  90                  95

Ser Ala Asp Arg Met Lys Glu Val Ala Thr Leu Ile Leu Ser Phe Pro
            100                 105                 110

Glu Glu Arg Pro Ile Val Val Leu Ser Ala Met Gly Lys Thr Thr Asn
            115                 120                 125

Lys Leu Leu Leu Ala Gly Glu Lys Ala Val Ser Cys Gly Val Ile Asn
        130                 135                 140

Val Ser Ser Ile Glu Glu Leu Cys Phe Ile Lys Asp Leu His Leu Arg
145                 150                 155                 160

Thr Val Asp Gln Leu Gly Val Asp Gly Ser Val Ile Ser Lys His Leu
                165                 170                 175

Glu Glu Leu Glu Gln Leu Leu Lys Gly Ile Ala Met Met Lys Glu Leu
            180                 185                 190

Thr Lys Arg Thr Gln Asp Tyr Leu Val Ser Phe Gly Glu Cys Met Ser
        195                 200                 205

Thr Arg Ile Phe Ala Ala Tyr Leu Asn Lys Ile Gly Val Lys Ala Arg
    210                 215                 220

Gln Tyr Asp Ala Phe Glu Ile Gly Phe Ile Thr Thr Asp Asp Phe Thr
225                 230                 235                 240

Asn Ala Asp Ile Leu Glu Ala Thr Tyr Pro Ala Val Ala Lys Arg Leu
                245                 250                 255
```

-continued

His Gly Asp Trp Leu Ser Asp Pro Ala Ile Ala Ile Val Thr Gly Phe
            260                 265                 270

Leu Gly Lys Ala Arg Lys Ser Cys Ala Val Thr Thr Leu Gly Arg Gly
        275                 280                 285

Gly Ser Asp Leu Thr Ala Thr Thr Ile Gly Lys Ala Leu Gly Leu Pro
        290                 295                 300

Glu Ile Gln Val Trp Lys Asp Val Asp Gly Val Leu Thr Cys Asp Pro
305                 310                 315                 320

Asn Ile Tyr Pro Lys Ala Glu Pro Val Pro Tyr Leu Thr Phe Asp Glu
                325                 330                 335

Ala Ala Glu Leu Ala Tyr Phe Gly Ala Gln Val Leu His Pro Gln Ser
            340                 345                 350

Met Arg Pro Ala Arg Glu Ser Asp Ile Pro Val Arg Val Lys Asn Ser
        355                 360                 365

Tyr Asn Pro Lys Ala Pro Gly Thr Leu Ile Thr Lys Ala Arg Asp Met
    370                 375                 380

Ser Lys Ala Val Leu Thr Ser Ile Val Leu Lys Arg Asn Val Thr Met
385                 390                 395                 400

Leu Asp Ile Ala Ser Thr Arg Met Leu Gly Gln Tyr Gly Phe Leu Ala
                405                 410                 415

Lys Val Phe Ser Ile Phe Glu Glu Leu Gly Ile Ser Val Asp Val Val
            420                 425                 430

Ala Thr Ser Glu Val Ser Val Ser Leu Thr Leu Asp Pro Ser Lys Leu
        435                 440                 445

Trp Ser Arg Glu Leu Ile Gln Gln Ala Ser Glu Leu Asp His Val Val
    450                 455                 460

Glu Glu Leu Glu Lys Ile Ala Val Val Asn Leu Leu Gln Asn Arg Ser
465                 470                 475                 480

Ile Ile Ser Leu Ile Gly Asn Val Gln Arg Ser Ser Leu Ile Leu Glu
                485                 490                 495

Arg Leu Ser Arg Val Leu Arg Thr Leu Gly Val Thr Val Gln Met Ile
            500                 505                 510

Ser Gln Gly Ala Ser Lys Val Asn Ile Ser Leu Val Val Asn Asp Ser
        515                 520                 525

Glu Ala Glu Gln Cys Val Arg Ala Leu His Ser Ala Phe Phe Glu Ser
    530                 535                 540

Glu Leu Ser Glu Leu Glu Met Asp Tyr Lys Asn Gly Asn Gly Ser Val
545                 550                 555                 560

Asp Glu Leu Ser

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 18
ctctctgcca tgggaa                                                17

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:Synthetic -continued oligonucleotide

<400> SEQUENCE: 19
gactggtacc tcagcccacg agtaggt                                              27

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 20
gactccatgg agggattggg gga                                                  23

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 21
gttttcccca tggcagaga                                                       19

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 22
ttagtgtttc tgtgttactt gatccatcaa ag                                        32

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 23
ctttgatgga tcaagtaaca cagaaacact aac                                       33

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 24
gactccatgg caatcccagt gcg                                                  23

<210> SEQ ID NO 25
<211> LENGTH: 11
<212> TYPE: PRT
<213> ORGANISM: Zea maize
<220> FEATURE:
<223> OTHER INFORMATION: DOMAIN -continued

```
<400> SEQUENCE: 25

Thr Ser Glu Val Ser Val Ser Val Ser Leu Asp
  1               5                  10

<210> SEQ ID NO 26
<211> LENGTH: 11
<212> TYPE: PRT
<213> ORGANISM: Escherichia coli
<220> FEATURE:
<223> OTHER INFORMATION: DOMAIN

<400> SEQUENCE: 26

Thr Ser Glu Val Ser Val Ala Leu Thr Leu Asp
  1               5                  10

<210> SEQ ID NO 27
<211> LENGTH: 12
<212> TYPE: PRT
<213> ORGANISM: Zea maize
<220> FEATURE:
<223> OTHER INFORMATION: DOMAIN

<400> SEQUENCE: 27

Ser Ser Arg Met Leu Gly Gln Tyr Gly Phe Leu Ala
  1               5                  10

<210> SEQ ID NO 28
<211> LENGTH: 12
<212> TYPE: PRT
<213> ORGANISM: Escherichia coli
<220> FEATURE:
<223> OTHER INFORMATION: DOMAIN

<400> SEQUENCE: 28

Ser Leu Asn Met Leu His Ser Arg Gly Phe Leu Ala
  1               5                  10
```

US 6,861,575 B2

ASPARTATE KINASE

This application claims the benefit of U.S. Provisional Application No. 60/172,944, filed Dec. 21, 1999.

FIELD OF THE INVENTION

This invention is in the field of plant molecular biology. More specifically, this invention pertains to nucleic acid fragments encoding aspartate kinase in plants and seeds.

BACKGROUND OF THE INVENTION

Many vertebrates, including man, lack the ability to manufacture a number of amino acids and therefore require these amino acids preformed in the diet. These are called essential amino acids. Human food and animal feed, derived from many grains, are deficient in essential amino acids, such as lysine, the sulfur amino acids methionine and cysteine, threonine and tryptophan. For example, in corn (*Zea mays* L.) lysine is the most limiting amino acid for the dietary requirements of many animals. Soybean (*Glycine max* L.) meal is used as an additive to corn-based animal feeds primarily as a lysine supplement. Thus, an increase in the lysine content of either corn or soybean would reduce or eliminate the need to supplement mixed grain feeds with lysine produced via fermentation of microbes. Furthermore, in corn the sulfur amino acids are the third most limiting amino acids, after lysine and tryptophan, for the dietary requirements of many animals. The use of soybean meal, which is rich in lysine and tryptophan, to supplement corn in animal feed is limited by the low sulfur amino acid content of the legume. Thus, an increase in the sulfur amino acid content of either corn or soybean would improve the nutritional quality of the mixtures and reduce the need for further supplementation through addition of more expensive methionine.

Efforts to improve the sulfur amino acid content of crops through plant breeding have met with limited success on the laboratory scale and no success on the commercial scale. A mutant corn line which had an elevated whole-kernel methionine concentration was isolated from corn cells grown in culture by selecting for growth in the presence of inhibitory concentrations of lysine plus threonine [Phillips et al., *Cereal Chem.*, (1985), 62, 213–218]. However, agronomically-acceptable cultivars have not yet been derived from this line and commercialized. Soybean cell lines with increased intracellular concentrations of methionine were isolated by selection for growth in the presence of ethionine [Madison and Thompson, *Plant Cell Reports*, (1988), 7, 472–476], but plants were not regenerated from these lines.

Lysine, threonine, methionine, cysteine and isoleucine are amino acids derived from aspartate. One approach to increasing the nutritional quality of human foods and animal feed is to increase the production and accumulation of specific free amino acids via genetic engineering of the biosynthetic pathway that leads from aspartate to lysine, threonine, methionine, cysteine and isoleucine. However, few of the genes encoding enzymes that regulate this pathway in plants, especially corn, soybeans and wheat, are available. Alteration of the activity of enzymes in this pathway could lead to altered levels of lysine, threonine, methionine, cysteine and isoleucine. For instance, recombinant DNA and gene transfer technologies have been applied to alter enzyme activity at key steps in the amino acid biosynthetic pathway. The introduction into plants of a feedback-regulation-insensitive dihydrodipicolinic acid synthase ("DHDPS") gene, which encodes an enzyme that catalyzes the first reaction unique to the lysine biosynthetic pathway, has resulted in an increase in the levels of free lysine in the leaves and seeds of those plants (Falco, U.S. Pat. No. 5,773,691; Glassman, U.S. Pat. No. 5,258,300). Also, expression in plants of a bacterial lysC gene with aspartate kinase activity has resulted in an increase in threonine content of the seed (Karchi, et al. *The Plant J.* 3:721–727 (1993); Galili, et al., European Patent Application No. 0485970). However, expression of the lysC gene results in only a 6–7% increase in the level of total threonine or methionine in the seed; thus, feed containing lysC transgenic seeds still requires amino acid supplementation.

The organization of the pathway leading to biosynthesis of lysine, threonine, methionine, cysteine and isoleucine indicates that over-expression or reduction of expression of several genes encoding key regulatory enzymes of the pathway in corn, soybean, wheat and other crop plants could be used to alter levels of these amino acids in human food and animal feed. For example, methionine, along with threonine, lysine and isoleucine, are amino acids derived from aspartate. The first step in the pathway is the phosphorylation of aspartate by the enzyme aspartate kinase (Tang et al. (1997) *Plant Mol Biol* 34:287–293; Frankard et al. (1997) *Plant Mol Biol* 34:233–242), and this enzyme has been found to be an important target for regulation of the pathway in many organisms. The aspartate family pathway is also believed to be regulated at the branch-point reactions. For methionine the reduction of aspartyl β-semialdehyde by homoserine dehydrogenase (HDH) may be an important point of control. Some aspartate kinases only carry aspartate kinase activity, in which case they are referred to as monofunctional, whereas there are bifunctional proteins found in bacteria and plants that carry both aspartate kinase and homoserine dehydrogenase enzymatic activities in two separate domains on one polypeptide. The first committed step to methionine, the production of cystathionine from O-phosphohomoserine and cysteine by cystathionine γ-synthase (CS), appears to be an important point of control of flux through the methionine pathway [Giovanelli et al., *Plant Physiol.*, (1984), 77, 450–455]. The final step in methionine biosynthesis is catalyzed by the enzyme 5-methyltetrahydropteroyltriglutamate-homocysteine methyltransferase, also known as methionine synthase. Accordingly, availability of nucleic acid sequences encoding all or a portion of aspartate kinase would facilitate development of nutritionally improved crop plants.

SUMMARY OF THE INVENTION

The present invention concerns an isolated polynucleotide comprising: (a) a first nucleotide sequence encoding a first polypeptide comprising at least 50 or 100 amino acids, wherein the amino acid sequence of the first polypeptide and the amino acid sequence of SEQ ID NO:10 have at least 95% identity based on the Clustal alignment method, (b) a second nucleotide sequence encoding a second polypeptide comprising at least 95 or 100 amino acids, wherein the amino acid sequence of the second polypeptide and the amino acid sequence of SEQ ID NO:2 have at least 90% or 95% identity based on the Clustal alignment method, (c) a third nucleotide sequence encoding a third polypeptide comprising at least 100 amino acids, wherein the amino acid sequence of the third polypeptide and the amino acid sequence of SEQ ID NO:4 have at least 70%, 80%, 85%, 90%, or 95% identity based on the Clustal alignment method, (d) a fourth nucleotide sequence encoding a fourth polypeptide comprising at least 100 amino acids, wherein the amino acid sequence of the fourth polypeptide and the amino acid sequence of SEQ ID NO:14 have at least 80%, 85%, 90%, or 95% identity based on the Clustal alignment method, (e) a fifth nucleotide sequence encoding a fifth polypeptide comprising at least 250 amino acids, wherein the amino acid sequence of the fifth polypeptide and the amino acid sequence of SEQ ID NO:12 have at least 80%, 85%, 90%, or 95% identity based on the Clustal alignment method, (f) a sixth nucleotide sequence encoding a sixth polypeptide comprising at least 400 amino acids, wherein the amino acid sequence of the sixth polypeptide and the amino acid sequence of SEQ ID NO:6 or SEQ ID NO:8 have at least 85%, 90%, or 95% identity based on the Clustal alignment method, (g) a seventh nucleotide sequence encoding a seventh polypeptide comprising at least 400 amino acids, wherein the amino acid sequence of the seventh polypeptide and the amino acid sequence of SEQ ID NO:16 have at least 90% or 95% identity based on the Clustal alignment method, or (h) the complement of the first, second, third, fourth, fifth, sixth, or seventh nucleotide sequence, wherein the complement and the first, second, third, fourth, fifth, sixth, or seventh nucleotide sequence contain the same number of nucleotides and are 100% complementary. The first polypeptide preferably comprises the amino acid sequence of SEQ ID NO:10, the second polypeptide preferably comprises the amino acid sequence of SEQ ID NO:2, the third polypeptide preferably comprises the amino acid sequence of SEQ ID NO:4, the fourth polypeptide preferably comprises the amino acid sequence of SEQ ID NO:14, the fifth polypeptide preferably comprises the amino acid sequence of SEQ ID NO:12, the sixth polypeptide preferably comprises the amino acid sequence of SEQ ID NO:6 or SEQ ID NO:8, and the seventh polypeptide preferably comprises the amino acid sequence of SEQ ID NO:16. The first nucleotide sequence preferably comprises the nucleotide sequence of SEQ ID NO:9, the second nucleotide sequence preferably comprises the nucleotide sequence of SEQ ID NO:1, the third nucleotide sequence preferably comprises the nucleotide sequence of SEQ ID NO:3, the fourth nucleotide sequence preferably comprises the nucleotide sequence of SEQ ID NO:13, the fifth nucleotide sequence preferably comprises the nucleotide sequence of SEQ ID NO:11, the sixth nucleotide sequence preferably comprises the nucleotide sequence of SEQ ID NO:5 or SEQ ID NO:7, and the seventh nucleotide sequence preferably comprises the nucleotide sequence of SEQ ID NO:15. The first, second, third, fourth, fifth, sixth, and seventh polypeptides preferably are aspartate kinases.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, or 60 nucleotides.

In a fifth embodiment, the present invention concerns an isolated polypeptide comprising: (a) a first amino acid sequence comprising at least 50 or 100 amino acids, wherein the first amino acid sequence and the amino acid sequence of SEQ ID NO:10 have at least 95% identity based on the Clustal alignment method, (b) a second amino acid sequence comprising at least 95 or 100 amino acids, wherein the second amino acid sequence and the amino acid sequence of SEQ ID NO:2 have at least 90% or 95% identity based on the Clustal alignment method, (c) a third amino acid sequence comprising at least 100 amino acids, wherein the third amino acid sequence and the amino acid sequence of SEQ ID NO:4 have at least 70%, 80%, 85%, 90%, or 95% identity based on the Clustal alignment method, (d) a fourth amino acid sequence comprising at least 100 amino acids, wherein the fourth amino acid sequence and the amino acid sequence of SEQ ID NO:14 have at least 80%, 85%, 90%, or 95% identity based on the Clustal alignment method, (e) a fifth amino acid sequence comprising at least 250 amino acids, wherein the fifth amino acid sequence and the amino acid sequence of SEQ ID NO:12 have at least 80%, 85%, 90%, or 95% identity based on the Clustal alignment method, (f) a sixth amino acid sequence comprising at least 400 amino acids, wherein the sixth amino acid sequence and the amino acid sequence of SEQ ID NO:6 or SEQ ID NO:8 have at least 85%, 90%, or 95% identity based on the Clustal alignment method, or (g) a seventh amino acid sequence comprising at least 400 amino acids, wherein the seventh amino acid sequence and the amino acid sequence of SEQ ID NO:16 have at least 90% or 95% identity based on the Clustal alignment method. The first amino acid sequence preferably comprises the amino acid sequence of SEQ ID NO:10, the second amino acid sequence preferably comprises the amino acid sequence of SEQ ID NO:2, the third amino acid sequence preferably comprises the amino acid sequence of SEQ ID NO:4, the fourth amino acid sequence preferably comprises the amino acid sequence of SEQ ID NO:14, the fifth amino acid sequence preferably comprises the amino acid sequence of SEQ ID NO:12, the sixth amino acid sequence preferably comprises the amino acid sequence of SEQ ID NO:6 or SEQ ID NO:8, and the seventh amino acid sequence preferably comprises the amino acid sequence of SEQ ID NO:16. The polypeptide preferably is an aspartate kinase.

In a sixth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a seventh embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In an eighth embodiment, the present invention relates to a virus, preferably a baculovirus, comprising any of the isolated polynucleotides of the present invention or any of the chimeric genes of the present invention.

In a ninth embodiment, the invention relates to a method of selecting an isolated polynucleotide that affects the level of expression of an aspartate kinase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the aspartate kinase polypeptide or enzyme activity in the host cell containing the isolated polynucleotide; and (d) comparing the level of the aspartate kinase polypeptide or enzyme activity in the host cell containing the isolated polynucleotide with the level of the aspartate kinase polypeptide or enzyme activity in the host cell that does not contain the isolated polynucleotide.

In a tenth embodiment, the invention concerns a method of obtaining a nucleic acid fragment encoding a substantial portion of an aspartate kinase polypeptide, preferably a plant aspartate kinase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, and 15, and the complement of such nucleotide sequences; and amplifying a nucleic acid fragment (preferably a cDNA inserted in a cloning vector) using the oligonucleotide primer. The amplified nucleic acid fragment preferably will encode a substantial portion of an aspartate kinase polypeptide amino acid sequence.

In an eleventh embodiment, this invention relates to a method of obtaining a nucleic acid fragment encoding all or a substantial portion of the amino acid sequence encoding an aspartate kinase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the aspartate kinase polynucleotide in an amount sufficient to complement a null mutant to provide a positive selection means.

In a thirteenth embodiment, this invention relates to a method of altering the level of expression of an aspartate kinase in a host cell comprising: (a) transforming a host cell with a chimeric gene of the present invention; and (b) growing the transformed host cell under conditions that are suitable for expression of the chimeric gene wherein expression of the chimeric gene results in production of altered levels of the aspartate kinase in the transformed host cell.

In a fourteenth embodiment, this invention relates to a method of generating an aspartate kinase variant that has reduced sensitivity to inhibition by lysine and the variant produced by this method.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A and 1B shows an alignment of the amino acid sequences of aspartate kinase encoded by nucleotide sequences derived from corn clone cho1c.pk002.k6 (SEQ ID NO:6), corn clone cpd1c.pk010.k1 (SEQ ID NO:8), and *Glycine max* (NCBI GenBank Identifier (GI) No. 5305740; SEQ ID NO:17). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs or PCR fragment sequence ("Contig*"), or sequences encoding the entire protein derived from an FIS, a contig, or an FIS and PCR fragment sequence ("CGS"). Nucleotide SEQ ID NOs:3, 9, and 13 correspond to nucleotide SEQ ID NOs:1, 3, and 5, respectively, presented in U.S. Provisional Application No. 60/172,944, filed Dec. 21, 1999. Amino acid SEQ ID NOs:4, 10, and 14 correspond to amino acid SEQ ID NOs:2, 4, and 6, respectively, presented in U.S. Provisional Application No. 60/172,944, filed Dec. 21, 1999. The sequence descriptions and Sequence Listing attached hereto comply with the rules governing nucleotide and/or amino acid sequence disclosures in patent applications as set forth in 37 C.F.R. §1.821–1.825.

TABLE 1

Aspartate Kinase

| Protein (Plant Source) | Clone Designation | Status | SEQ ID NO: (Nucleotide) | SEQ ID NO: (Amino Acid) |
|---|---|---|---|---|
| Aspartate Kinase (Corn) | bms1.pk0008.e5 | FIS | 1 | 2 |
| Aspartate Kinase (Corn) | cho1c.pk002.k6 | EST | 3 | 4 |
| Aspartate Kinase (Corn) | cho1c.pk002.k6 (FIS) | CGS | 5 | 6 |
| Aspartate Kinase (Corn) | cpd1c.pk010.k1 (FIS) | CGS | 7 | 8 |
| Aspartate Kinase (Rice) | rdr1f.pk005.f20 | EST | 9 | 10 |
| Aspartate Kinase (Rice) | rdr1f.pk005.f20 | FIS | 11 | 12 |
| Aspartate Kinase (Wheat) | wr1.pk0046.b11 | EST | 13 | 14 |
| Aspartate Kinase (Wheat) | wr1.pk0046.b11 | FIS | 15 | 16 |

SEQ ID NO:17 sets forth the amino acid sequence of a precursor monofunctional aspartate kinase from *Glycine max* (NCBI GI No. 5305740).

SEQ ID NOS:18–21 are PCR primers used to amplify portions of the cDNA insert in clone cpd1c.pk010.k1 to create an aspartate-kinase-encoding construct for expression in *E. coli*.

SEQ ID NOS:22 and 23 are PCR primers used to introduce a site-specific mutation to change S (serine) to L (leucine) in the corn mono functional aspartate kinase as described in Example 8.

SEQ ID NO:24 is a PCR primer which was used with SEQ ID NO:21 to generate a 380 bp PCR fragment which has Nco I sites on both ends and contains the 5' end of the coding sequence including the plant chloroplast targeting sequence.

SEQ ID NO: 25 is Region 1 of the corn monofunctional Aspartate kinase described in Example 8.

SEQ ID NO: 26 is the Region 1 of the E.coli monofunctional Aspartate kinase described in Example 8.

SEQ ID NO: 27 is the Region 2 in the corn monofunctional Aspartate kinase described in Example 8.

SEQ ID NO: 28 is the Region 2 in the E.coli monofunctional Aspartate kinase described in Example 8.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J*. 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, or 15, or the complement of such sequences.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, and 15, and the complement of such nucleotide sequences may be used in methods of selecting an isolated polynucleotide that affects the expression of an aspartate kinase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6x SSC, 0.5% SDS at room temperature for 15 min, then repeated with 2x SSC, 0.5% SDS at 45° C. for 30 min, and then repeated twice with 0.2x SSC, 0.5% SDS at 50° C. for 30 min. A more preferred set of stringent conditions uses higher temperatures in which the washes are identical to those above except for the temperature of the final two 30 min washes in 0.2x SSC, 0.5% SDS was increased to 60° C. Another preferred set of highly stringent conditions uses two final washes in 0.1x SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 95 or at least 100 amino acids, more preferably at least 150 amino acids, still more preferably at least 200 amino acids, and most preferably at least 250 or at least 400 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial " portions of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410;). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portions" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising: (a) a first nucleotide sequence encoding a first polypeptide comprising at least 50 or 100 amino acids, wherein the amino acid sequence of the first polypeptide and the amino acid sequence of SEQ ID NO:10 have at least 95% identity based on the Clustal alignment method, (b) a second nucleotide sequence encoding a second polypeptide comprising at least 95 or 100 amino acids, wherein the amino acid sequence of the second polypeptide and the amino acid sequence of SEQ ID NO:2 have at least 90% or 95% identity based on the Clustal alignment method, (c) a third nucleotide sequence encoding a third polypeptide comprising at least 100 amino acids, wherein the amino acid sequence of the third polypeptide and the amino acid sequence of SEQ ID NO:4 have at least 70%, 80%, 85%, 90%, or 95% identity based on the Clustal alignment method, (d) a fourth nucleotide sequence encoding a fourth polypeptide comprising at least 100 amino acids, wherein the amino acid sequence of the fourth polypeptide and the amino acid sequence of SEQ ID NO:14 have at least 80%, 85%, 90%, or 95% identity based on the Clustal alignment method, (e) a fifth nucleotide sequence encoding a fifth polypeptide comprising at least 250 amino acids, wherein the amino acid sequence of the fifth polypeptide and the amino acid sequence of SEQ ID NO:12 have at least 80%, 85%, 90%, or 95% identity based on the Clustal alignment method, (f) a sixth nucleotide sequence encoding a sixth polypeptide comprising at least 400 amino acids, wherein the amino acid sequence of the sixth polypeptide and the amino acid sequence of SEQ ID NO:6 or SEQ ID NO:8 have at least 85%, 90%, or 95% identity based on the Clustal alignment method, (g) a seventh nucleotide sequence encoding a seventh polypeptide comprising at least 400 amino acids, wherein the amino acid sequence of the seventh polypeptide and the amino acid sequence of SEQ ID NO:16 have at least 90% or 95% identity based on the Clustal alignment method, or (h) the complement of the first, second, third, fourth, fifth, sixth, or seventh nucleotide sequence, wherein the complement and the first, second, third, fourth, fifth, sixth, or seventh nucleotide sequence contain the same number of nucleotides and are 100% complementary. The first polypeptide preferably comprises the amino acid sequence of SEQ ID NO:10, the second polypeptide preferably comprises the amino acid sequence of SEQ ID NO:2, the third polypeptide preferably comprises the amino acid sequence of SEQ ID NO:4, the fourth polypeptide preferably comprises the amino acid sequence of SEQ ID NO:14, the fifth polypeptide preferably comprises the amino acid sequence of SEQ ID NO:12, the sixth polypeptide preferably comprises the amino acid sequence of SEQ ID NO:6 or SEQ ID NO:8, and the seventh polypeptide preferably comprises the amino acid sequence of SEQ ID NO:16. The first nucleotide sequence preferably comprises the nucleotide sequence of SEQ ID NO:9, the second nucleotide sequence preferably comprises the nucleotide sequence of SEQ ID NO:1, the third nucleotide sequence preferably comprises the nucleotide sequence of SEQ ID NO:3, the fourth nucleotide sequence preferably comprises the nucleotide sequence of SEQ ID NO:13, the fifth nucleotide sequence preferably comprises the nucleotide sequence of SEQ ID NO:11, the sixth nucleotide sequence preferably comprises the nucleotide sequence of SEQ ID NO:5 or SEQ ID NO:7, and the seventh nucleotide sequence preferably comprises the nucleotide sequence of SEQ ID NO:15. The first, second, third, fourth, fifth, sixth, and seventh polypeptides preferably are aspartate kinases.

Nucleic acid fragments encoding at least a portion of several aspartate kinases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other aspartate kinases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) Proc. Natl. Acad. Sci. USA 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) Proc. Natl. Acad. Sci. USA 86:5673–5677; Loh et al. (1989) Science 243:217–220). Products generated by the 3' and 5' RACE procedures can be combined to generate full-length cDNAs (Frohman and Martin (1989) Techniques 1:165). Consequently, a polynucleotide comprising a nucleotide sequence of at least one of 60 preferably one of at least 40, most preferably one of at least 30) contiguous nucleotides derived from a nucleotide sequence selected from the group consisting of SEQ ID NOs:1, 3, 5, 7, 9, 11, 13, and 15, and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of an aspartate kinase polypeptide, preferably a substantial portion of a plant aspartate kinase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, and 15, and the complement of such nucleotide sequences; and amplifying a nucleic acid fragment (preferably a cDNA inserted in a cloning vector) using the oligonucleotide primer. The amplified nucleic acid fragment preferably will encode a portion of an aspartate kinase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of free amino acids (e.g., aspartate, threonine, lysine, and methionine) in those plants. Using these nucleic acid fragments that encode aspartate kinase, variants that have reduced sensitivity to lysine or another amino acid (e.g., threonine) may be generated by a variety of methods (e.g., the method described in U.S. Pat. No. 5,773,691) such that the aspartate kinase may continue to be active in the presence of high levels of lysine or another amino acid (e.g., threonine), leading to the accumulation of lysine and/or threonine in the seeds of transformed plants.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an isolated polypeptide comprising: (a) a first amino acid sequence comprising at least 50 or 100 amino acids, wherein the first amino acid sequence and the amino acid sequence of SEQ ID NO:10 have at least 95% identity based on the Clustal alignment method, (b) a second amino acid sequence comprising at least 95 or 100 amino acids, wherein the second amino acid sequence and the amino acid sequence of SEQ ID NO:2 have at least 90% or 95% identity based on the Clustal alignment method, (c) a third amino acid sequence comprising at least 100 amino acids, wherein the third amino acid sequence and the amino acid sequence of SEQ ID NO:4 have at least 70%, 80%, 85%, 90%, or 95% identity based on the Clustal alignment method, (d) a fourth amino acid sequence comprising at least 100 amino acids, wherein the fourth amino acid sequence and the amino acid sequence of SEQ ID NO:14 have at least 80%, 85%, 90%, or 95% identity based on the Clustal alignment method, (e) a fifth amino acid sequence comprising at least 250 amino acids, wherein the fifth amino acid sequence and the amino acid sequence of SEQ ID NO:12 have at least 80%, 85%, 90%, or 95% identity based on the Clustal alignment method, (f) a sixth amino acid sequence comprising at least 400 amino acids, wherein the sixth amino acid sequence and the amino acid sequence of SEQ ID NO:6 or SEQ ID NO:8 have at least 85%, 90%, or 95% identity based on the Clustal alignment method, or (g) a seventh amino acid sequence comprising at least 400 amino acids, wherein the seventh amino acid sequence and the amino acid sequence of SEQ ID NO:16 have at least 90% or 95% identity based on the Clustal alignment method. The first amino acid sequence preferably comprises the amino acid sequence of SEQ ID NO:10, the second amino acid sequence preferably comprises the amino acid sequence of SEQ ID NO:2, the third amino acid sequence preferably comprises the amino acid sequence of SEQ ID NO:4, the fourth amino acid sequence preferably comprises the amino acid sequence of SEQ ID NO:14, the fifth amino acid sequence preferably comprises the amino acid sequence of SEQ ID NO:12, the sixth amino acid sequence preferably comprises the amino acid sequence of SEQ ID NO:6 or SEQ ID NO:8, and the seventh amino acid sequence preferably comprises the amino acid sequence of SEQ ID NO:16. The polypeptide preferably is an aspartate kinase.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aspartate kinase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*), rice (*Oryza sativa*), and wheat (*Triticum aestivum*) tissues were prepared. The characteristics of the libraries are described below.

TABLE 2 cDNA Libraries from Corn, Rice, and Wheat

| Library | Tissue | Clone |
|---|---|---|
| bms1 | Corn (BMS) Cell Culture 1 Day After Subculture | bms1.pk0008.e5 |
| cho1c | Corn Embryo (Alexho Synthetic High Oil) 20 Days After Pollination | cho1c.pk002.k6 |
| cpd1c | Corn Pooled BMS Treated with Chemicals Related to Protein Kinases* | cpd1c.pk010.k1 |
| rdr1f | Developing Root of 10 Day Old Rice Plant | rdr1f.pk005.f20 |
| wr1 | Root From 7 Day Old Light Grown Wheat Seedling | wr1.pk0046.b11 |

*Chemicals used included 1,2-didecanoyl rac glycerol, straurosporine, K-252a, A3, H-7, olomoucine, and rapamycin, all of which are commercially available from Calbiochem-Novabiochem Corp. (1-800-628-8470)

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding aspartate kinase were identified by conducting BLAST (Basic Local Alignment Search Tool; Altschul et al. (1993) *J. Mol. Biol.* 215:403–410;) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtain in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3-prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Aspartate Kinase

The BLASTX search using the EST sequences from clones listed in Table 3 revealed similarity of the polypeptides encoded by the cDNAs to aspartate kinase from *Oryza sativa* (NCBI GenBank Identifier (GI) No. 7798569), *Arabidopsis thaliana* (NCBI GI Nos. 4376158 and 7529283), or *Glycine max* (NCBI GI No. 5305740). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to Aspartate Kinase

| Clone | Status | BLAST Results NCBI GI No. | pLog Score |
|---|---|---|---|
| cho1c.pk002.k6 | EST | 4376158 | 19.30 |
| rdr1f.pk005.f20 | EST | 5305740 | 54.70 |
| wr1.pk0046.b11 | EST | 5305740 | 48.70 |

The sequence of the entire cDNA insert in the clones listed in Table 3 was determined. Further sequencing and searching of the DuPont proprietary database allowed the identification of other corn clones encoding aspartate kinase. The BLASTX search using the EST sequences from clones listed in Table 4 revealed similarity of the polypeptides encoded by the cDNAs to aspartate kinase from *Oryza sativa* (NCBI GI No. 7798569), *Arabidopsis thaliana* (NCBI GI Nos. 4376158 and 7529283), or *Glycine max* (NCBI GI No. 5305740). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to Aspartate Kinase

| Clone | Status | BLAST Results NCBI GI No. | pLog Score |
|---|---|---|---|
| bms1.pk0008.e5 | FIS | 7798569 | 32.70 |
| cho1c.pk002.k6 (FIS) | CGS | 5305740 | >180.00 |
| cpd1c.pk010.k1 (FIS) | CGS | 5305740 | >180.00 |
| rdr1f.pk005.f20 | FIS | 7529283 | 100.00 |
| wr1.pk0046.b11 | FIS | 7529283 | >180.00 |

FIG. 1 presents an alignment of the amino acid sequences set forth in SEQ ID NOs:6 and 8 and the *Glycine max* sequence (NCBI GI No. 5305740; SEQ ID NO:17). The data in Table 5 represents a calculation of the percent identity of the amino acid sequences set forth in SEQ ID NOs:6 and 8 and the *Glycine max* sequence (NCBI GI No. 5305740; SEQ ID NO:17).

TABLE 5

Percent Identity of Amino Acid Sequences Deduced From the Nucleotide Sequences of cDNA Clones Encoding Polypeptides Homologous to Aspartate Kinase

| SEQ ID NO. | Percent Identity to NCBI GI No. 5305740; SEQ ID NO:17 |
|---|---|
| 6 | 66.4 |
| 8 | 68.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an aspartate kinase. These sequences represent the first corn, rice and wheat sequences encoding aspartate kinase known to Applicant.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB); Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Functional Analysis of Aspartate Kinase Encoded by Clone cpd1c.pk010.k1

High level expression of the corn mono-functional aspartate kinase cDNA in clone cpd1c.pk010.k1 was accomplished in *E. coli* using the commercially available expression vector pTrcHis from Invitrogen. The corn aspartate kinase cDNA in clone cpd1c.pk010.k1 was modified for insertion into the expression vectors using PCR.

Cloning monofunctional corn aspartate kinase into expression vectors required two steps. First, a portion of the corn mono-functional aspartate kinase cDNA in clone cpd1c.pk010.k1 was amplified via PCR using the following primers, to create a Kpn I site after the stop codon:

Oligo 1: 5'-CTCTCTGCCATGGGGAA-3' (SEQ ID NO:18)
Oligo 2: 5'-GACTGGTACCTCAGCCCACGAGTAGGT-3' (SEQ ID NO:19)

The resulting PCR fragment, designated PCR fragment 1, was digested with Nco I and Kpn I and ligated into pTrcHis cut with the same enzymes. Then a different portion of the corn mono-functional aspartate kinase cDNA in clone cpd1c.pk010.k1 was amplified via PCR using the following primers, to remove the chloroplast transit sequence and create a NcoI-NcoI fragment:

Oligo 9: 5'-GACTCCATGGAGGGATTGGGGGA-3' (SEQ ID NO:20)
Oligo 8: 5'-GTTTTCCCCATGGCAGAGA-3' (SEQ ID NO:21)

The resulting PCR fragment, designated PCR fragment 3, was digested with Nco I and ligated into the pTrcHis-based expression vector containing a portion of cpd1c.pk010.k1 cDNA described above that was also cut with Nco I. Insertion of the Nco I fragment in the proper orientation was determined by sequencing of the inserted DNA. The resulting plasmid with cDNA encoding full-length monofunctional corn aspartate kinase without chloroplast transit sequence in the pTrcHis vector was designated pBT994.

To establish that the cloned monofunctional corn aspartate kinase cDNA was functional, pBT994 was transformed into *E. coli* strain Gif106M1 (*E. coli* Genetic Stock Center strain CGSC-5074) which has mutations in each of the three *E. coli* aspartate kinase genes [Theze et al. (1974) *J. Bacteriol.* 117:133–143]. Because this strain lacks all aspartate kinase activity, it requires lysine, threonine and methionine for growth. M9 media [see Sambrook et al. (1989) *Molecular Cloning, A Laboratory Manual*, Cold Spring Harbor Laboratory Press], supplemented with the arginine, isoleucine and valine, also required for Gif106M1 growth, was used. In the pBT994 transformed strain the nutritional requirement for lysine, threonine and methionine was relieved demonstrating that the cloned monofunctional corn aspartate kinase cDNA encoded functional aspartate kinase.

Example 8

Generation of Corn Aspartate Kinase with Reduced Sensitivity to Lysine

In order to use the monofunctional corn aspartate kinase to increase the production of the amino acid end-products of the pathway, i.e. lysine, threonine and methionine, it was desirable to create a mutant form of the enzyme that is insensitive to inhibition by lysine. Two approaches to accomplish this have been used.

One method to create a lysine-resistant mutant corn monofunctional aspartate kinase relied on a procedure analogous to the procedure used previously, and described in U.S. Pat. No. 5,773,691, to select mutants in the *E. coli* lysC gene, which encodes *E. coli* monofunctional aspartate kinase.

Addition of lysine at a concentration of approximately 0.2 mM to the growth medium inhibits the growth of Gif106M1 transformed with pBT994. This inhibition is reversed by addition of threonine plus methionine to the growth media. These results indicated that corn monofunctional aspartate kinase could be inhibited by exogenously added lysine leading to starvation for the other amino acids derived from aspartate. This property of pBT994 transformed Gif106M1 was used to select for mutations that encode lysine-insensitive monofunctional corn aspartate kinase.

Single colonies of Gif106M1 transformed with pBT994 were picked and resuspended in 200 μL of a mixture of 100 μL 1% lysine plus 100 μL of M9 media. The entire cell suspension containing $10^7$14 $10^8$ cells was spread on a petri dish containing M9 media supplemented with the arginine, isoleucine, and valine. Sixteen petri dishes were thus prepared. From 1 to 20 colonies appeared on 11 of the 16 petri dishes. One or two colonies were picked and retested for lysine resistance and from this test several independent lysine-resistant clones were obtained. Plasmid DNA was prepared from eight of these and re-transformed into Gif106M1 to determine whether the lysine resistance determinant was plasmid-borne. Three of the eight plasmid DNAs yielded lysine-resistant colonies indicating that they carry mutations in corn monofunctional AK that make the enzyme less sensitive to lysine inhibition.

A second method used PCR mutagenesis to create a site-specific mutation in the corn monofunctional aspartate kinase gene that reduces the encoded enzyme's sensitivity to inhibition by L-lysine. The particular amino acid substitutions to yield lysine-insensitive monofunctional corn aspartate kinase were based upon the homology that was discovered between monofunctional corn aspartate kinase and monofunctional *E. coil* aspartate kinase. Specifically, In two regions where particular amino acid substitutions were known to yield lysine-insensitive monofunctional *E. coil* aspartate kinase (see U.S. Pat. No. 5773,691) the monofunctional corn spartate kinase was found to have similar amino acid sequence. These regions are shown below:

Region 1 monofunctional corn aspartate kinase TSEVSVSVSLD (SEQ ID NO:25)

monofunctional *E. coli* aspartate kinase TSEVSVAL<u>T</u>LD (SEQ ID NO:26)

The lysine-insensitive mutant monofunctional *E. coli* aspartate kinase has the underlined T (threonine) residue changed to I (isoleucine).

Region 2 monofunctional corn aspartate kinase SSRMLGQYG-FLA (SEQ ID NO:27)

monofunctional *E. coli* aspartate kinase SLN <u>M</u>LHSRGFLA (SEQ ID NO:28)

The lysine-insensitive mutant monofunctional *E. coli* aspartate kinase has the underlined M (methionine) residue changed to I (isoleucine).

A site-specific mutation to change S (serine) to L (leucine) in the corn monofunctional aspartate kinase at the position in Region 1 where a T (threonine) residue was changed to I (isoleucine) in monofunctional *E. coli* aspartate kinase was created using PCR mutagenesis as described below.

First, a 370 bp portion of the corn monofunctional aspartate kinase cDNA in clone cpd1c.pk010.k1 was amplified via PCR using Oligo 2 (SEQ ID NO:19) and Oligo 3 (SEQ ID NO:22) as primers:

Oligo 3: 5'-TTAGTGTTTCTGTGTTACTTGATCCATCA AAG-3' (SEQ ID NO:22)

Then a 980 bp portion of the corn monofunctional aspartate kinase cDNA in clone cpd1c.pk010.k1 was amplified via PCR using Oligo 1 (SEQ ID NO:18) and Oligo 6 (SEQ ID NO:23) as primers:

Oligo 6: 5'-CTTTGATGGATCAAGTAACACAGAAAC ACTAAC-3' (SEQ ID NO:23)

The 370 bp and 980 bp PCR fragments were then mixed together, denatured and allowed to hybridize heterologously.

Staggered ends were filled-in with Taq polymerase, and PCR was performed on the DNA mixture using Oligos 1 (SEQ ID NO:18) and 2 (SEQ ID NO:19) as primers. This generated a 1320 bp Nco I-Kpn I fragment, designated PCR fragment 6, with the desired mutation that changes S (serine) to L (leucine) in the corn monofunctional aspartate kinase.

The 1320 bp NcoI-KpnI fragment containing the lysine-resistant (i.e., reduced sensitivity to inhibition by lysine) mutant corn monofunctional aspartate kinase was digested with Nco I and Kpn I and ligated into pTrcHis cut with the same enzymes. PCR fragment 3 described in Example 7 was ligated into the resulting plasmid in the same way PCR fragments 1 and 3 were combined into a single plasmid described in Example 7. The creation of a mutant corn monofunctional aspartate kinase gene which contains a single nucleotide change compared to the native corn monofunctional aspartate kinase gene resulting in a change of amino acid 441 (in SEQ ID NO:8) from serine to leucine was confirmed by DNA sequencing. That the mutant corn monofunctional aspartate kinase gene encodes an enzyme with reduced sensitivity to inhibition by lysine was confirmed by in vivo testing as described below.

The mutant corn monofunctional aspartate kinase gene was inserted into the pTrcHis vector, as was done for the wild type corn monofunctional aspartate kinase gene, as described above. Plasmids carrying the mutant and wild type corn AK genes were transformed into Gif106M1 and tested for their ability to support growth in the absence or presence of exogenously added lysine. Both were able to support growth in the absence of exogenously added lysine, indicating that both mutant and wild type enzymes were expressed and functional. However, only the mutant corn monofunctional aspartate kinase gene was able to support growth in the presence of exogenously added lysine, indicating that the mutant enzyme was resistant to inhibition by lysine.

Example 9

Construction of Chimeric Aspartate Kinase Genes for Expression in Plants

A chimeric gene for overexpression of monofunctional corn aspartate kinase in the embryo of transformed corn was constructed. The globulin 1 promoter and 3' sequences were isolated from a Clontech corn genomic DNA library using oligonucleotide probes based on the published sequence of the globulin 1 gene [Kriz et al. (1989) *Plant Physiol.* 91:636]. The cloned segment includes the promoter fragment extending 1078 nucleotides upstream from the ATG translation start codon, the entire globulin coding sequence including introns and the 3' sequence extending 803 bases from the translational stop. To allow replacement of the globulin 1 coding sequence with other coding sequences an Nco I site was introduced at the ATG start codon, and Kpn I and Xba I sites were introduced following the translational stop codon via PCR to create vector pCC50. An Nco I site within the globulin 1 promoter fragment was then eliminated by partial digestion with Nco I followed by single strand exonuclease treatment to remove the single-stranded overhangs created by the Nco I digestion and then blunt end ligation creating plasmid pHD1. The globulin 1 gene cassette is flanked by Hind III sites.

To construct the chimeric gene:
globulin 1 promoter/monofunctional corn aspartate kinase/globulin 1 3'region
the 1320 base pair Nco I and Kpn I PCR fragment 1 (described in Example 7) containing the major part of the monofunctional corn aspartate kinase coding region was inserted into plasmid pHD1 between the globulin 1 5' and 3' regions creating pBT954. A 380 bp fragment, designated PCR fragment 2, which has Nco I sites on both ends and contains the amino end of the coding sequence including the plant chloroplast targeting sequence, was generated via PCR using oligo 7 (SEQ ID NO:24) and oligo 8 (SEQ ID NO:21) as primers:
oligo 7: 5'-GACTCCATGGCAATCCCAGTGCG-3' (SEQ ID NO:24)

PCR fragment 2 was digested with Nco I and ligated into pBT954. Insertion of 380 bp PCR fragment 2 in the proper orientation was determined by DNA sequencing, yielding the plant expression vector pBT960. Similarly, the 1320 base pair Nco I and Kpn I PCR fragment 6 (described in Example 8) containing the major part of the lysine-resistant mutant corn monofunctional aspartate kinase was inserted into plasmid pHD1 between the globulin 1 5' and 3' regions creating pBT955. Then 380 bp PCR fragment 2 (above), which contains the amino end of the coding sequence including the plant chloroplast targeting sequence, was digested with Nco I and ligated into pBT955. Insertion of 380 bp PCR fragment 2 in the proper orientation was determined by DNA sequencing, yielding the plant expression vector pBT961.

What is claimed is:

1. An isolated polynucleotide comprising:
   (a) a nucleotide sequence encoding a polypeptide having Aspartate kinase activity, wherein the polypeptide has an amino acid sequence of at least 90% sequence identity, based on the Clustal V method of alignment, when compared to SEQ ID NO: 6 or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide has at least 95% sequence identity, based on the Clustal V method of alignment, when compared to SEQ ID NO: 6.

3. The polynucleotide of claim 1, wherein the amino acid sequence of the polypeptide comprises SEQ ID NO:6.

4. The polynucleotide of claim 1 wherein the nucleotide sequence comprises SEQ ID NO: 5.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

12. A method for isolating a polypeptide encoded by he polynucleotide of claim 1 comprising expressing and isolating the polypeptide from a cell containing a recombinant DNA construct comprising the polynucleotide operably linked to a regulatory sequence.

* * * * *